United States Patent [19]
Kriesel et al.

[11] Patent Number: 6,126,637
[45] Date of Patent: Oct. 3, 2000

[54] FLUID DELIVERY DEVICE WITH COLLAPSIBLE NEEDLE COVER

[75] Inventors: Marshall S. Kriesel, St. Paul; Thomas N. Thompson, Richfield, both of Minn.

[73] Assignee: Science Incorporated, Bloomington, Minn.

[21] Appl. No.: 09/061,087

[22] Filed: Apr. 15, 1998

[51] Int. Cl.$^7$ .................................................. A61M 37/00
[52] U.S. Cl. ........................ 604/132; 604/890.1; 604/93; 604/198
[58] Field of Search .................. 604/890.1, 892.1, 604/93, 256, 246, 115, 162, 163, 244, 132, 198, 199, 192, 93.01; 128/DIG. 12

[56] References Cited

U.S. PATENT DOCUMENTS

| | | | |
|---|---|---|---|
| 4,592,745 | 6/1986 | Rex et al. . | |
| 4,850,994 | 7/1989 | Zerbst et al. . | |
| 4,892,521 | 1/1990 | Laico et al. | 604/192 |
| 4,935,013 | 6/1990 | Haber et al. | 604/192 |
| 4,950,250 | 8/1990 | Haber et al. . | |
| 5,015,240 | 5/1991 | Soproni et al. | 604/192 |
| 5,070,886 | 12/1991 | Mitchen et al. | 128/771 |
| 5,205,820 | 4/1993 | Kriesel et al. . | |
| 5,226,896 | 7/1993 | Harris . | |
| 5,267,974 | 12/1993 | Lambert | 604/195 |
| 5,290,254 | 3/1994 | Vaillancourt . | |
| 5,334,197 | 8/1994 | Kriesel et al. | 604/132 |
| 5,492,533 | 2/1996 | Kriesel | 604/132 |
| 5,656,032 | 8/1997 | Kriesel et al. | 604/132 |
| 5,693,018 | 12/1997 | Kriesel et al. | 604/132 |
| 5,695,474 | 12/1997 | Daugherty . | |
| 5,735,818 | 4/1998 | Kriesel et al. | 604/132 |
| 5,779,676 | 7/1998 | Kriesel et al. | 604/132 |
| 5,961,492 | 10/1999 | Kriesel et al. | 604/132 |

FOREIGN PATENT DOCUMENTS

| | | |
|---|---|---|
| WO96/11026 | 4/1996 | WIPO . |
| WO97/21457 | 6/1997 | WIPO . |

*Primary Examiner*—Corrine McDermott
*Assistant Examiner*—Cris L. Rodriguez
*Attorney, Agent, or Firm*—James E. Brunton

[57] ABSTRACT

A fluid delivery device having a self-contained stored energy membrane for defining in conjunction with a base a fluid reservoir and for expelling fluids from the reservoir. The device includes novel reservoir filling syringe and filling adapter for conveniently filling the fluid reservoir of the device. Additionally, the device includes a unique crushable or collapsible needle cover which surrounds and protects the infusion cannula until time of use and then readily deforms as the device is connected to the patient so as to permit the needle to cleanly penetrate the patient's skin. The needle cover maintains the cannula in a substantially aseptic condition and enables self-administration by patients, such as young patients or needle adverse patients, which does not require their consciously inserting a needle into the skin.

18 Claims, 17 Drawing Sheets

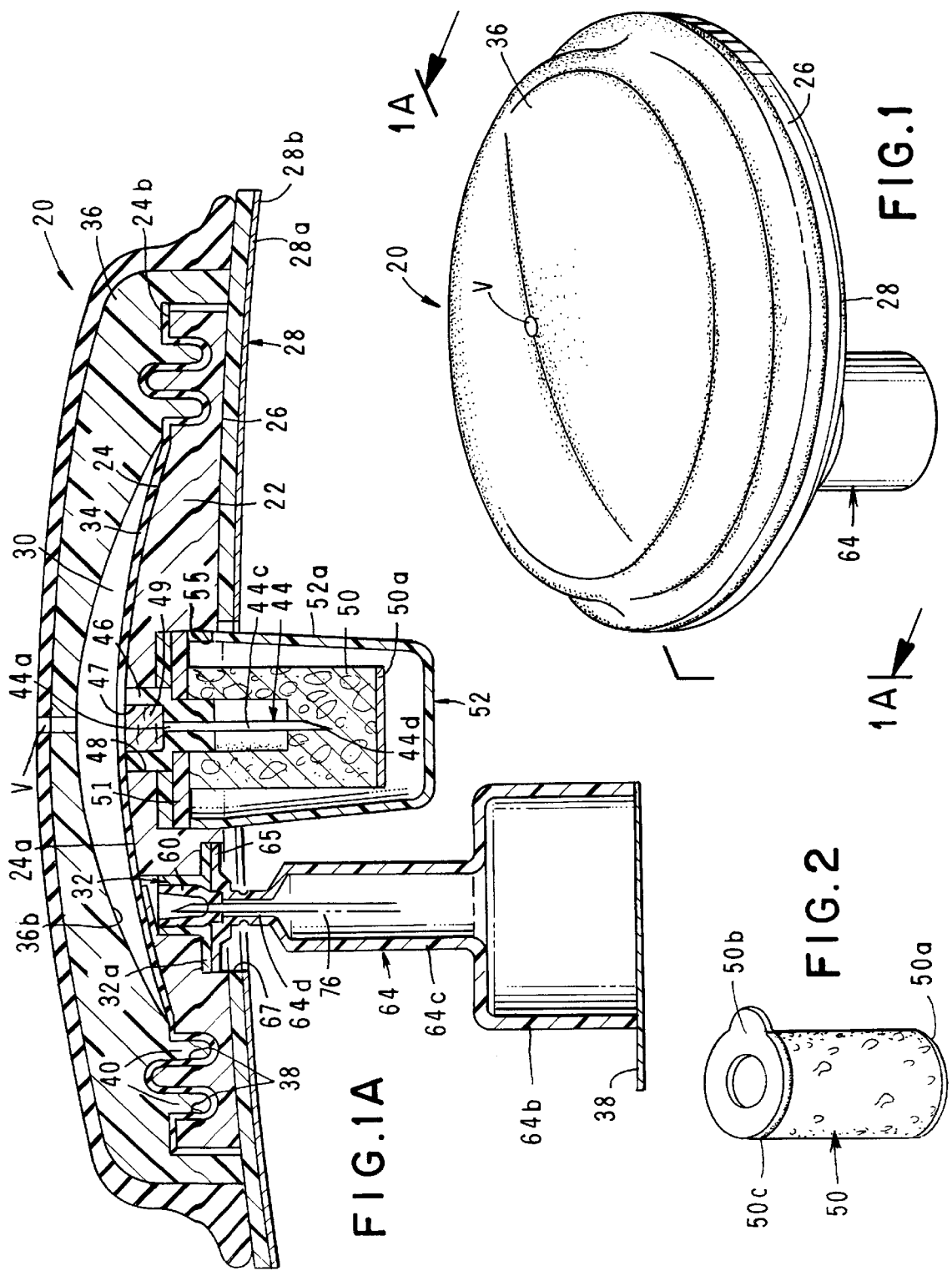

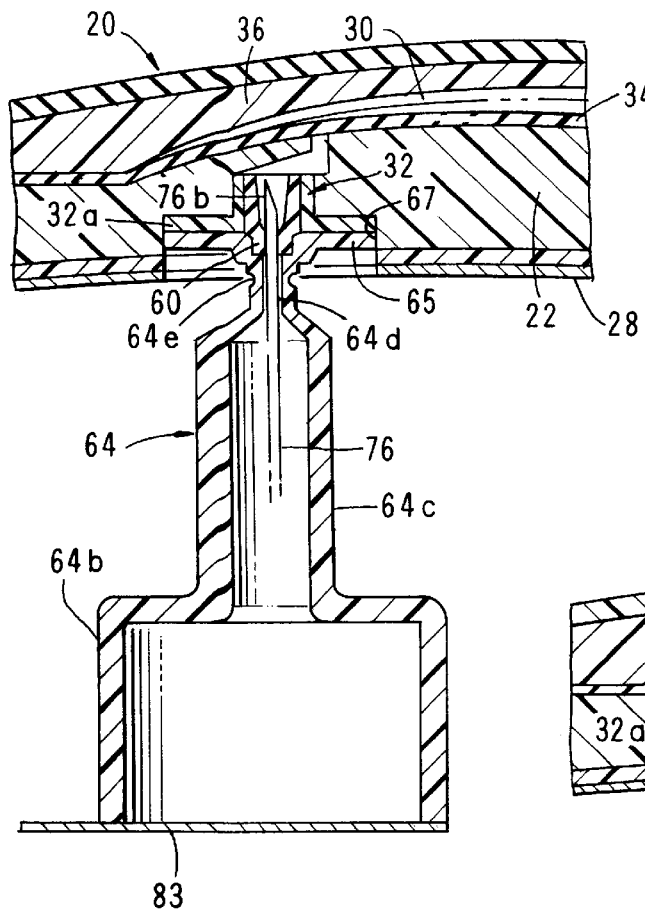
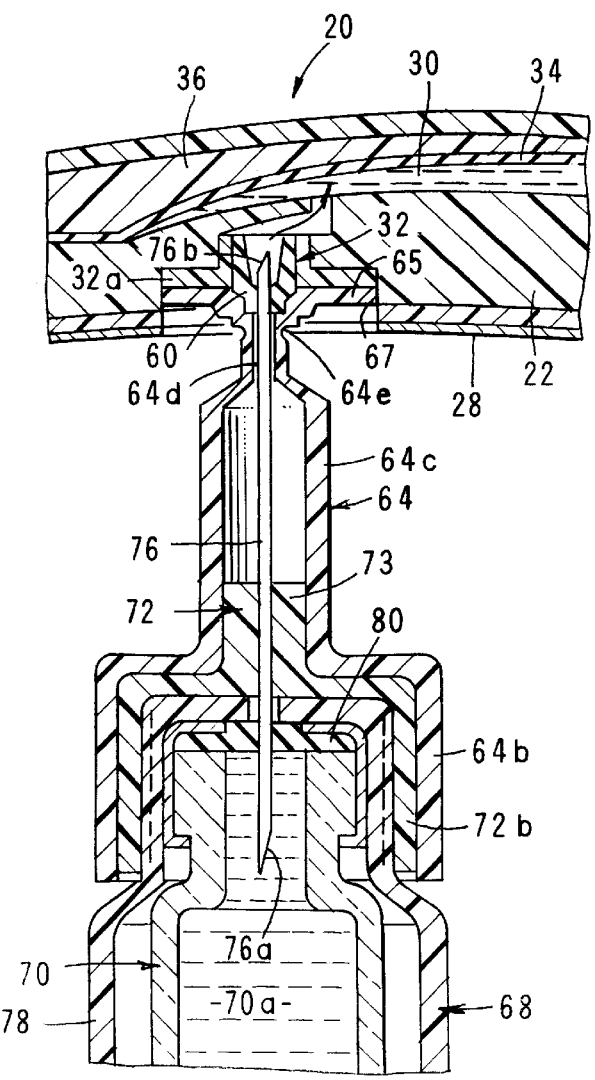
FIG. 3
FIG. 4

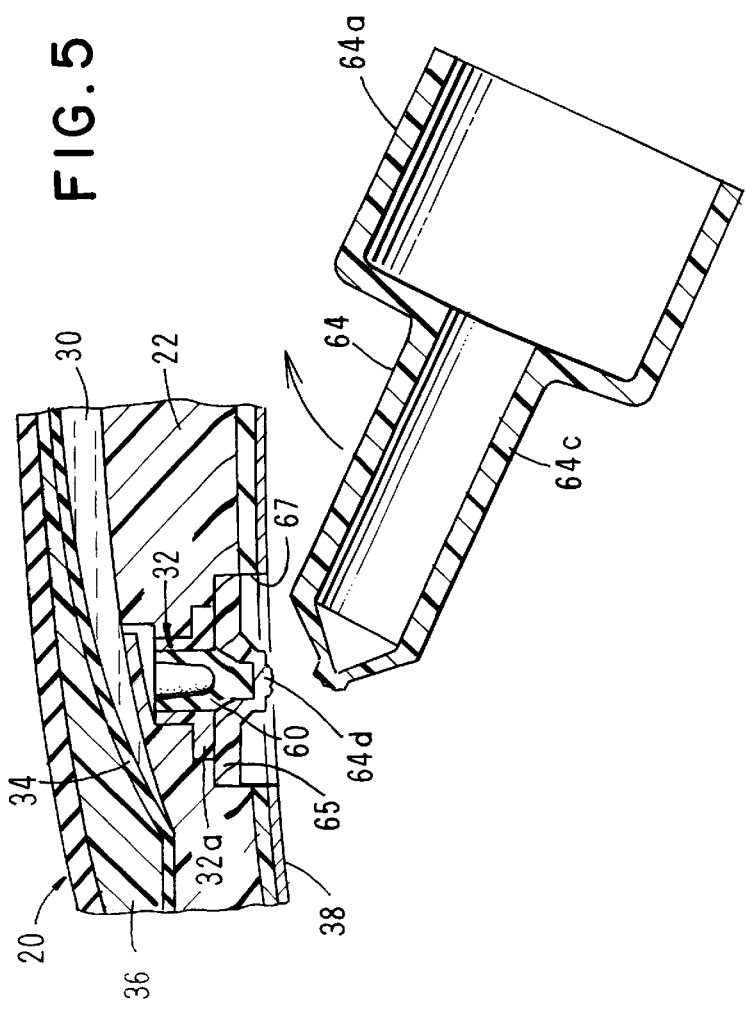
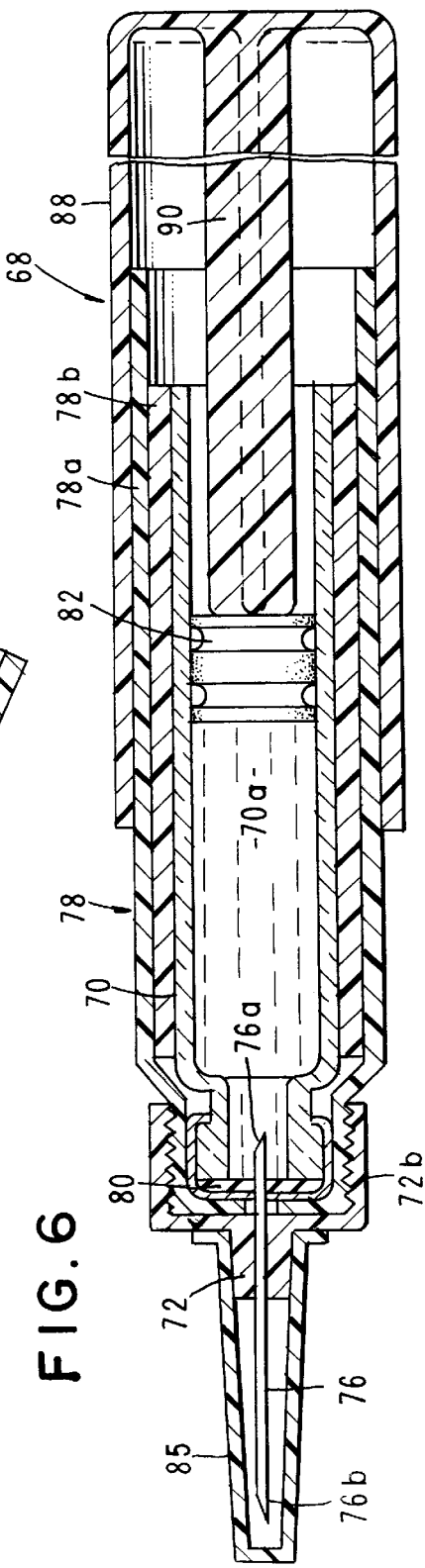

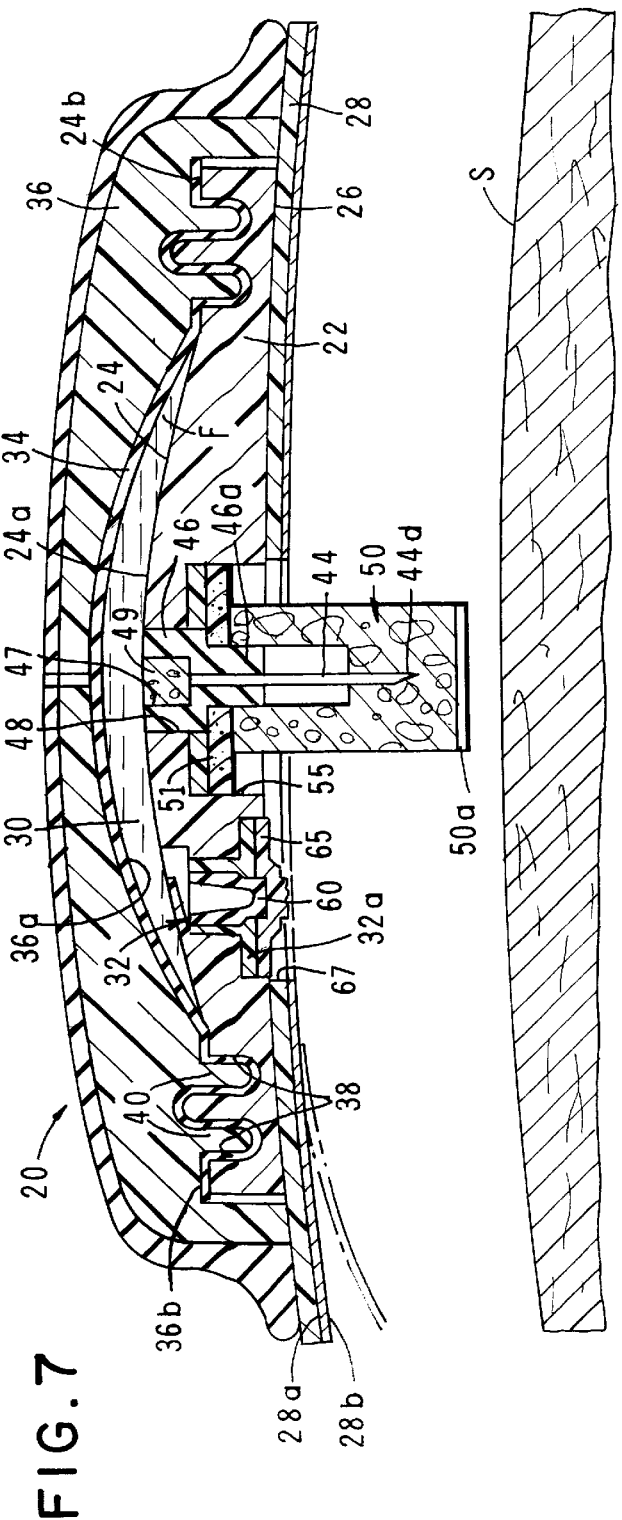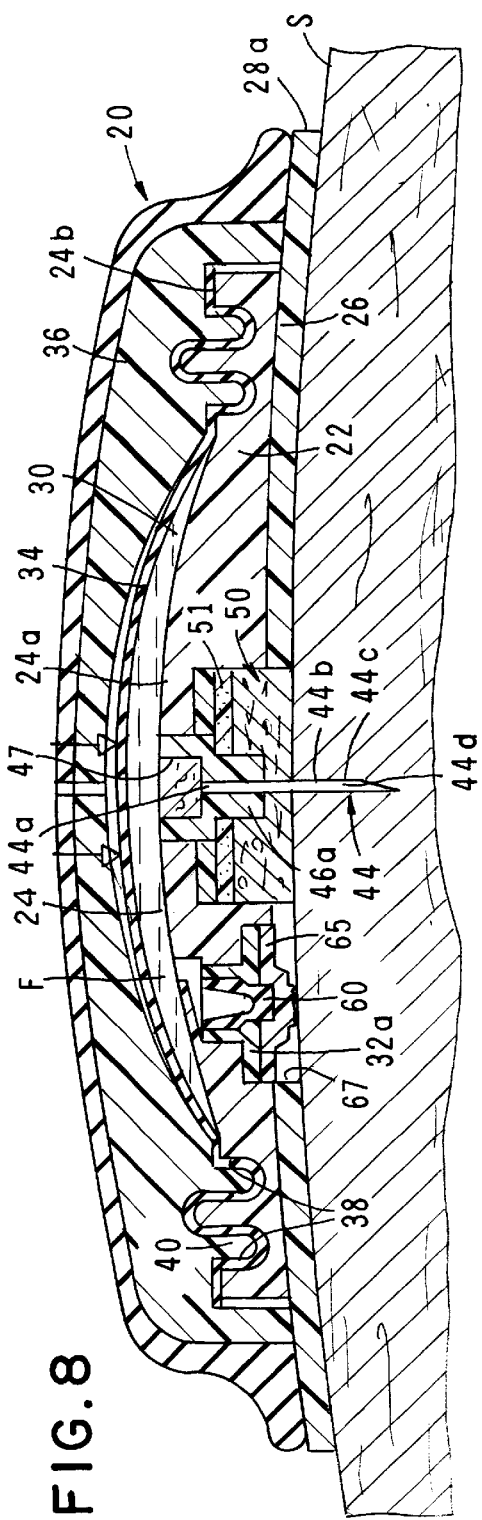

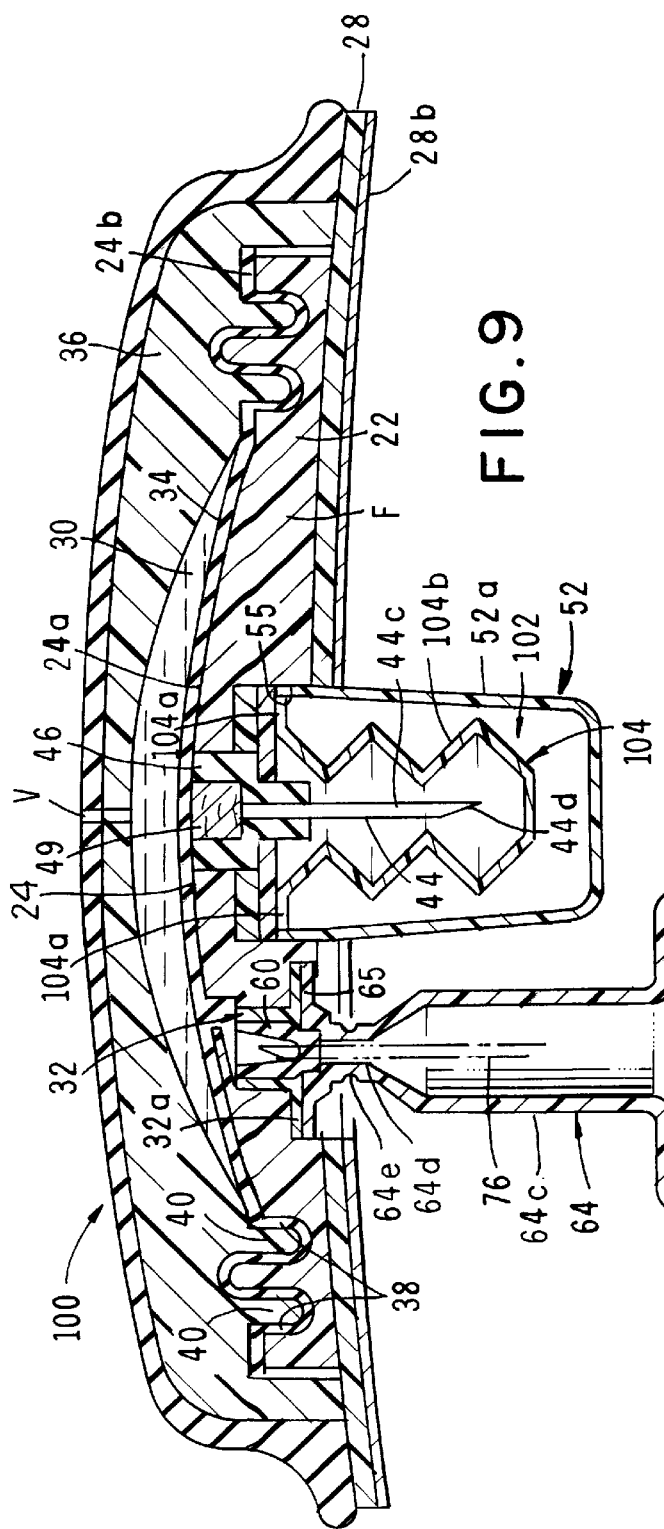

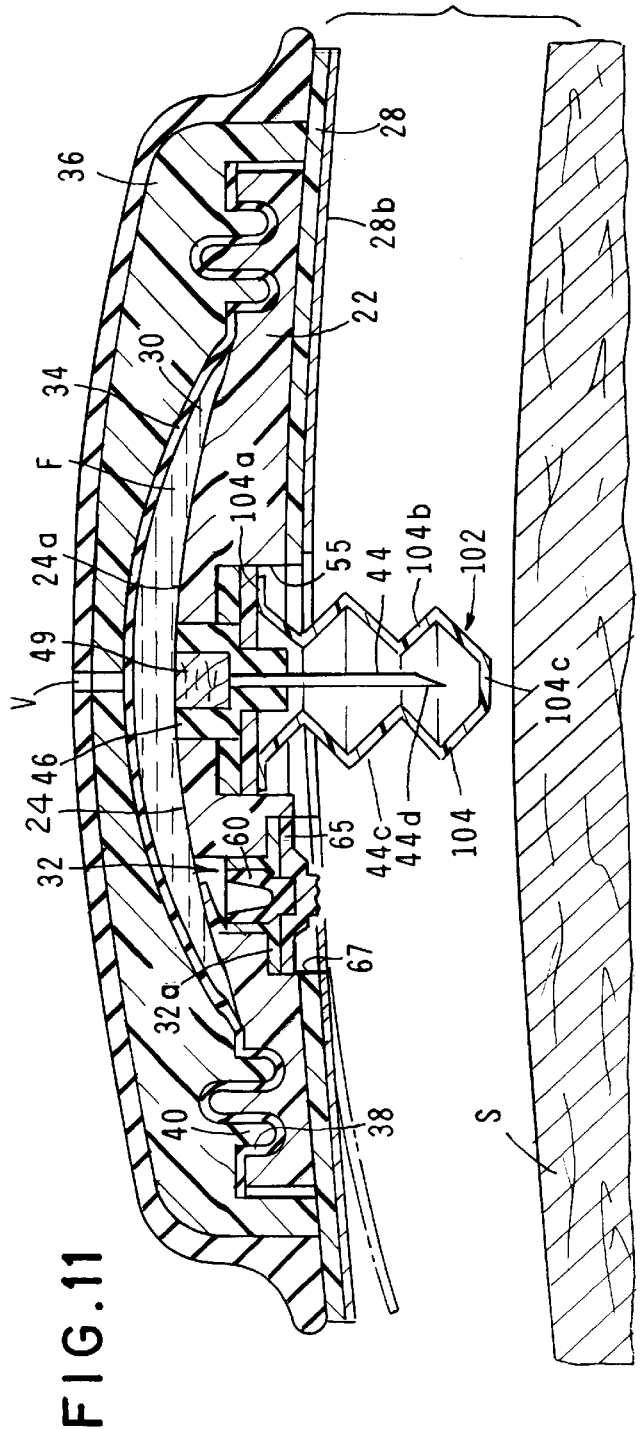
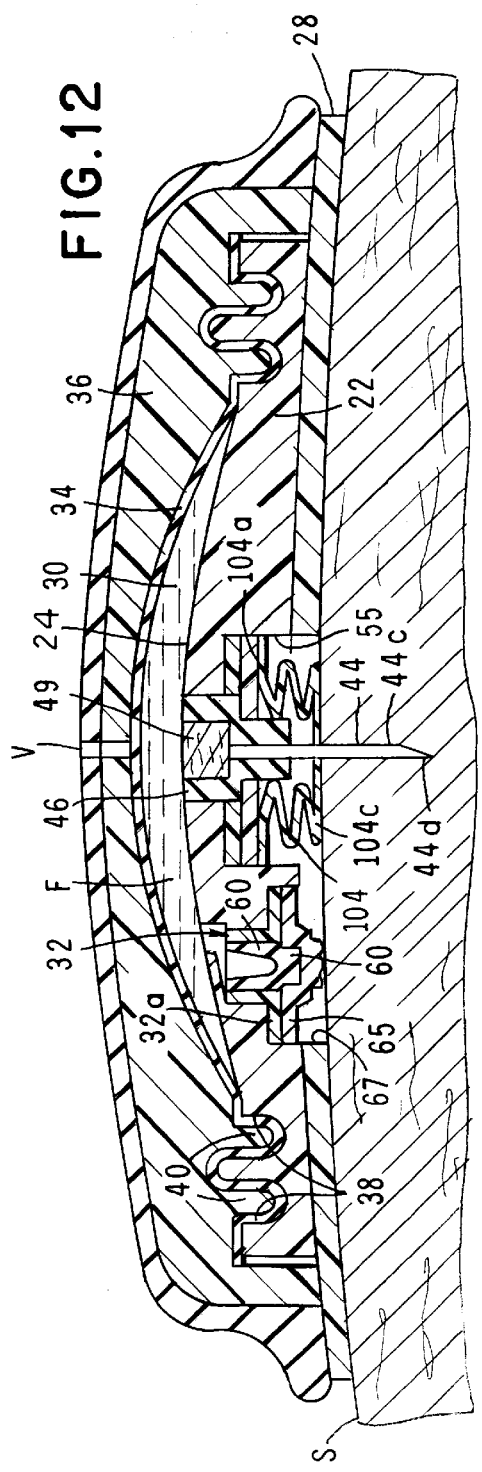

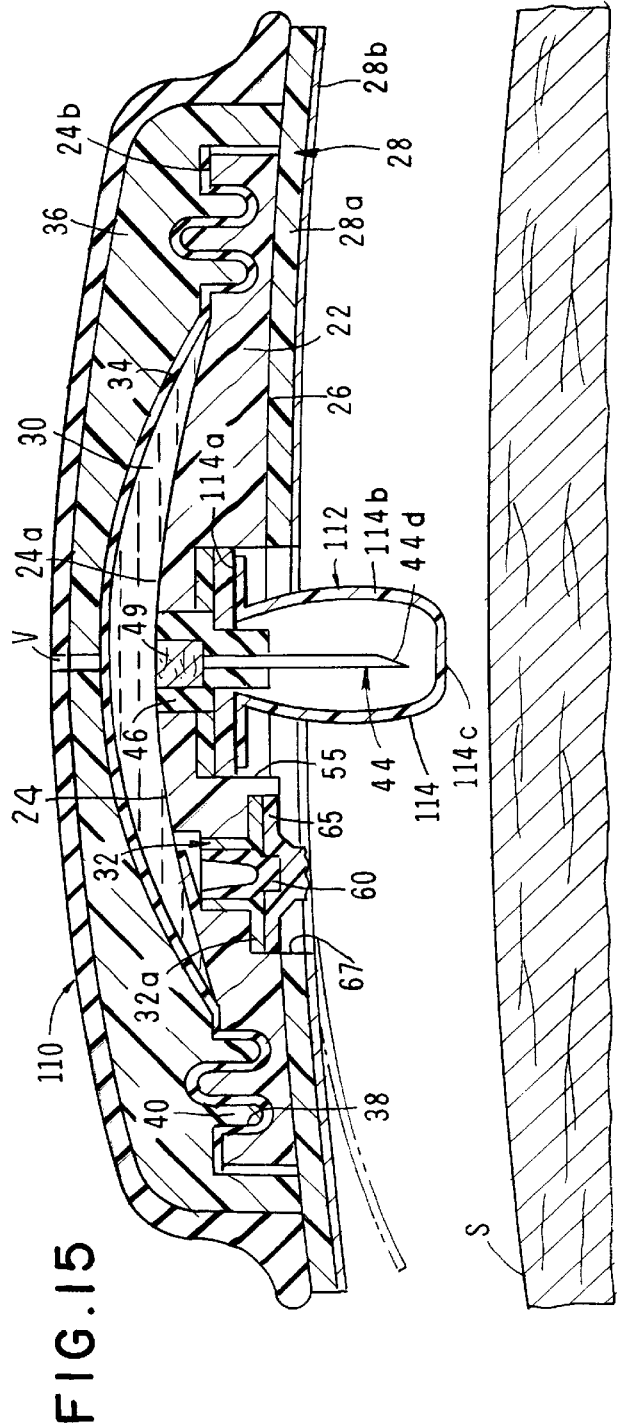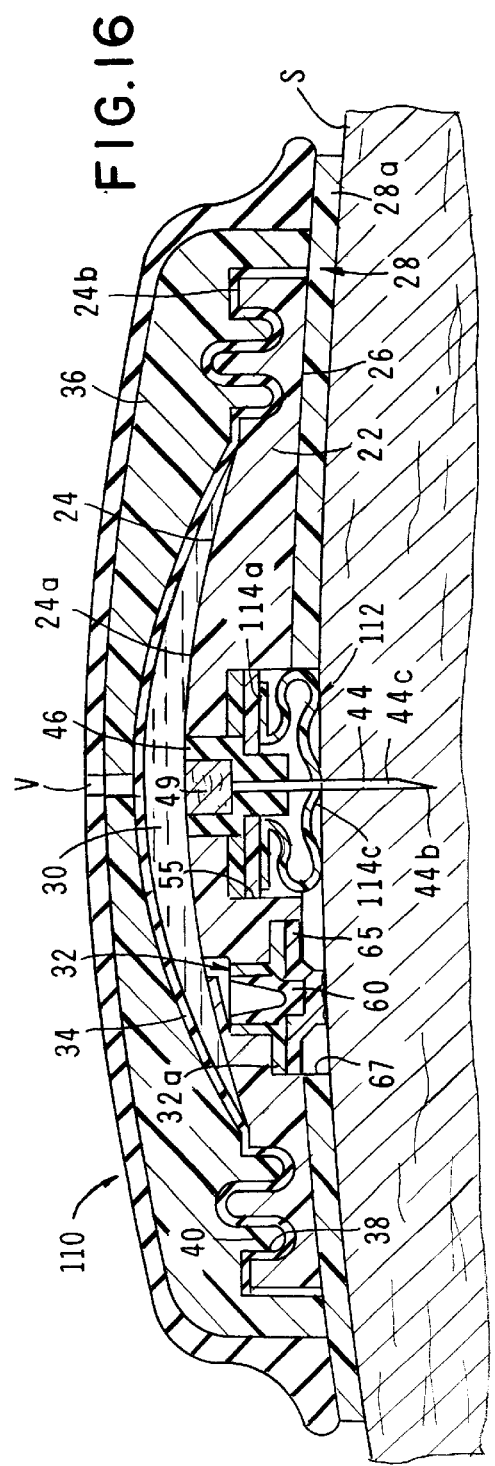

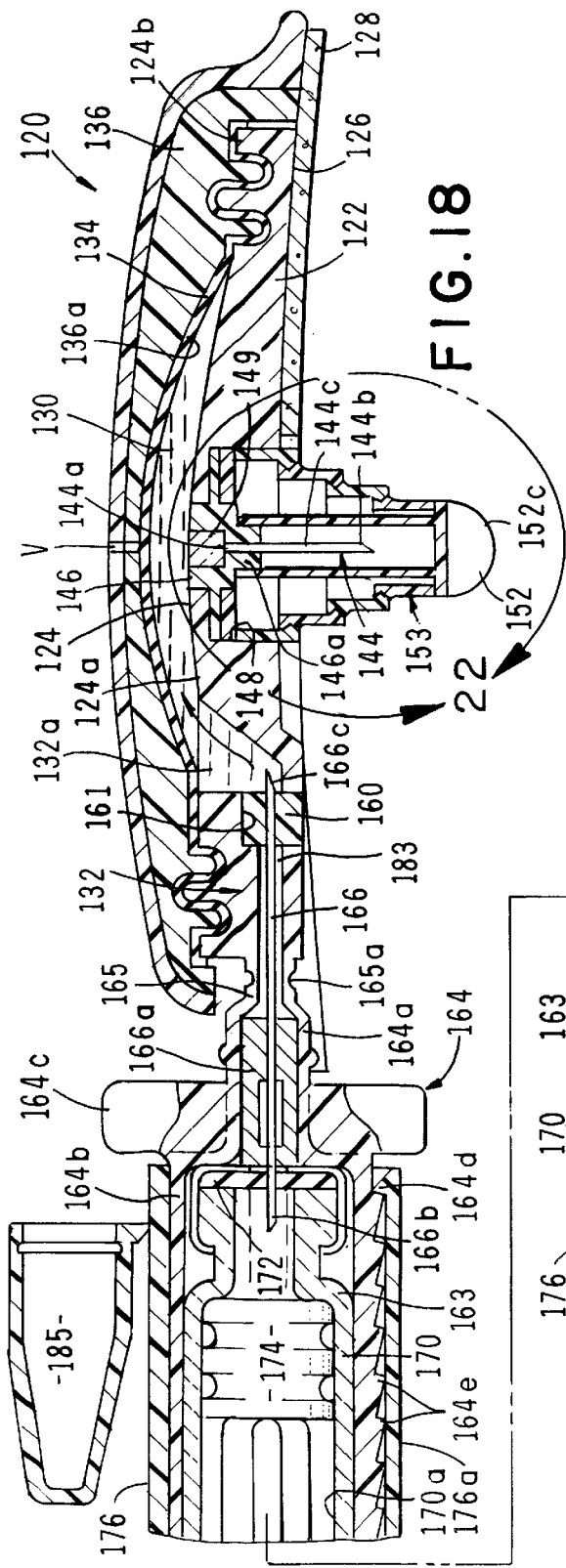
FIG. 18
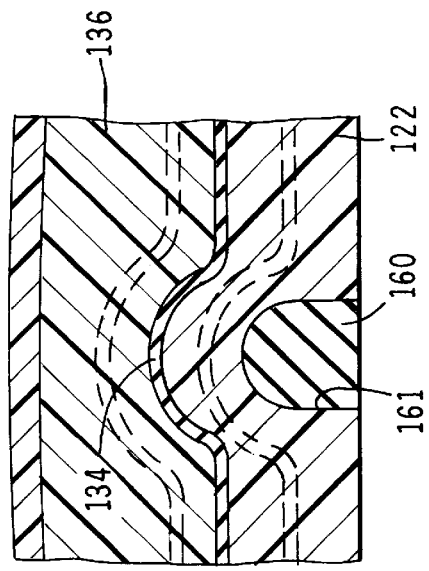
FIG. 20
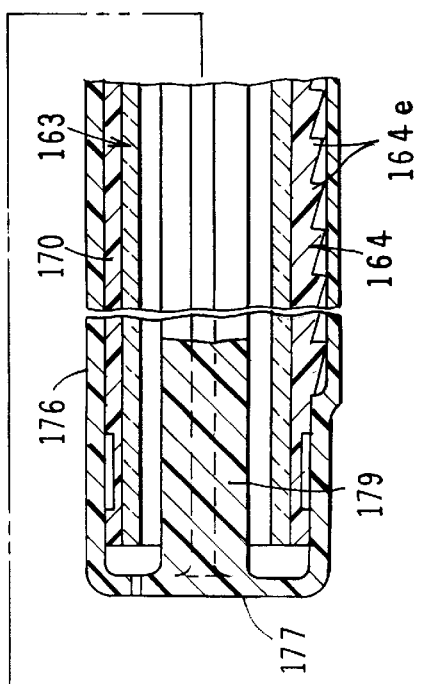

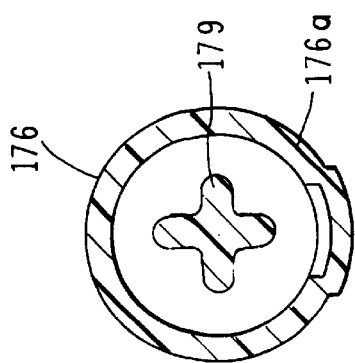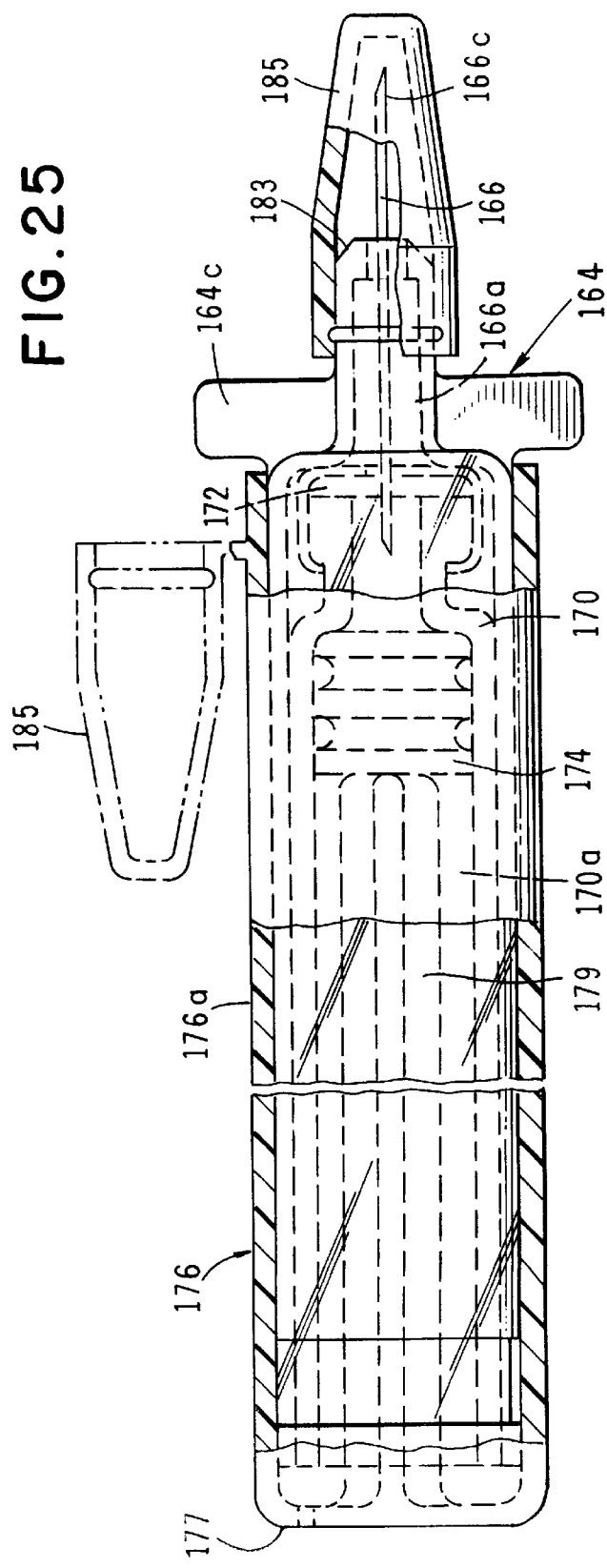

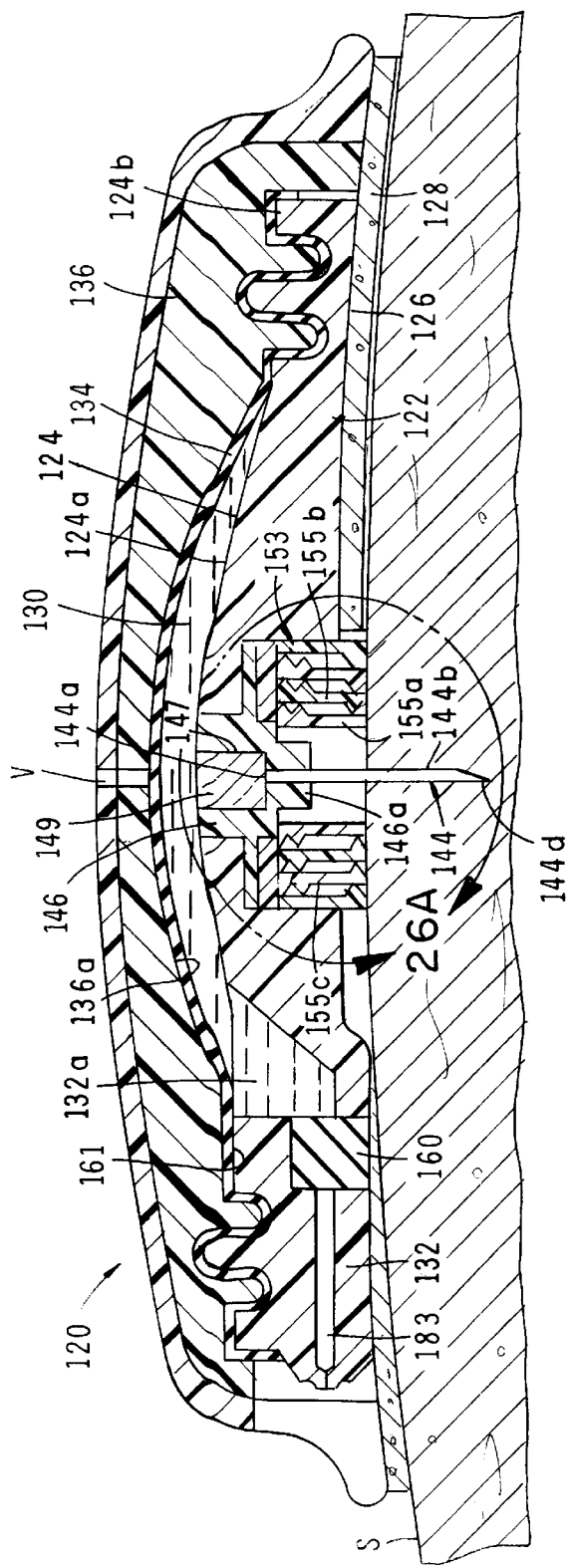
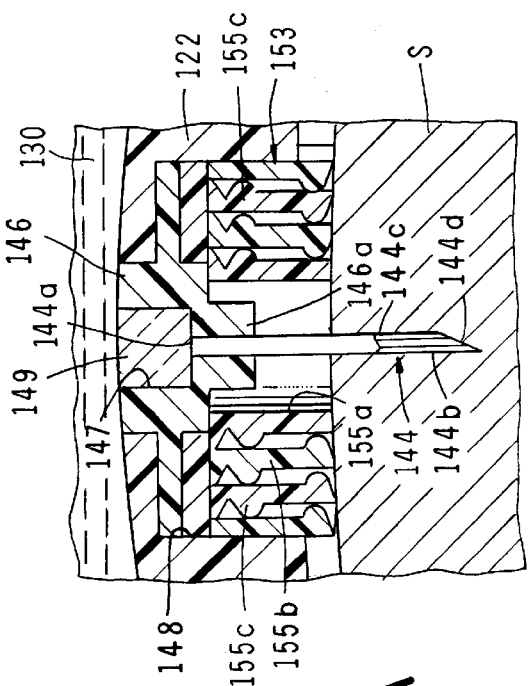
FIG. 26
FIG. 26A

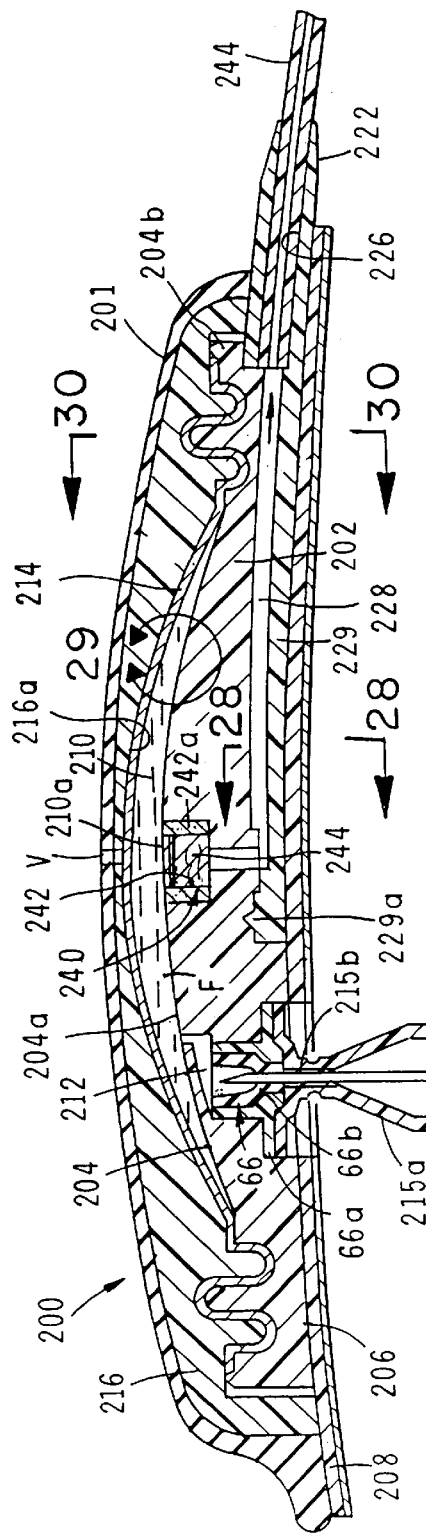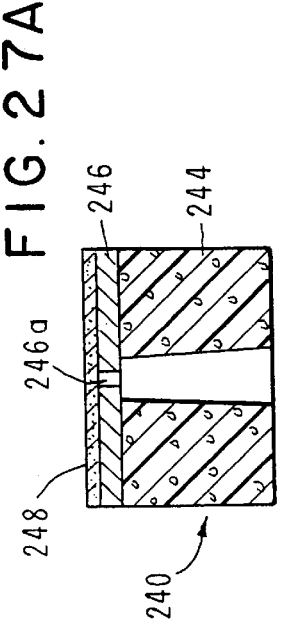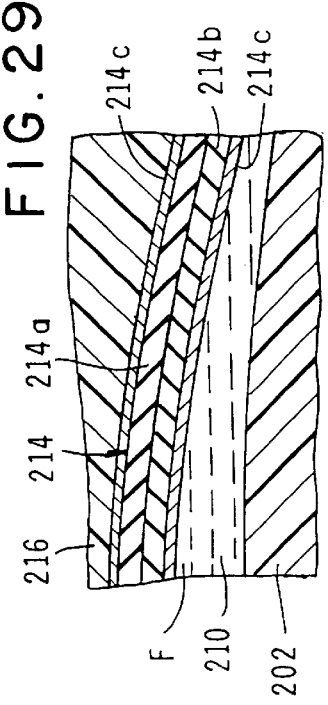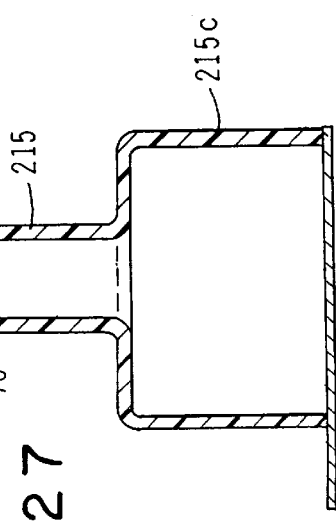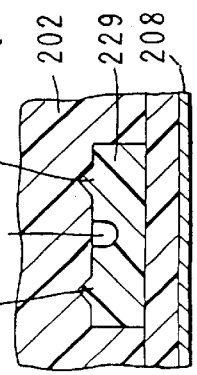

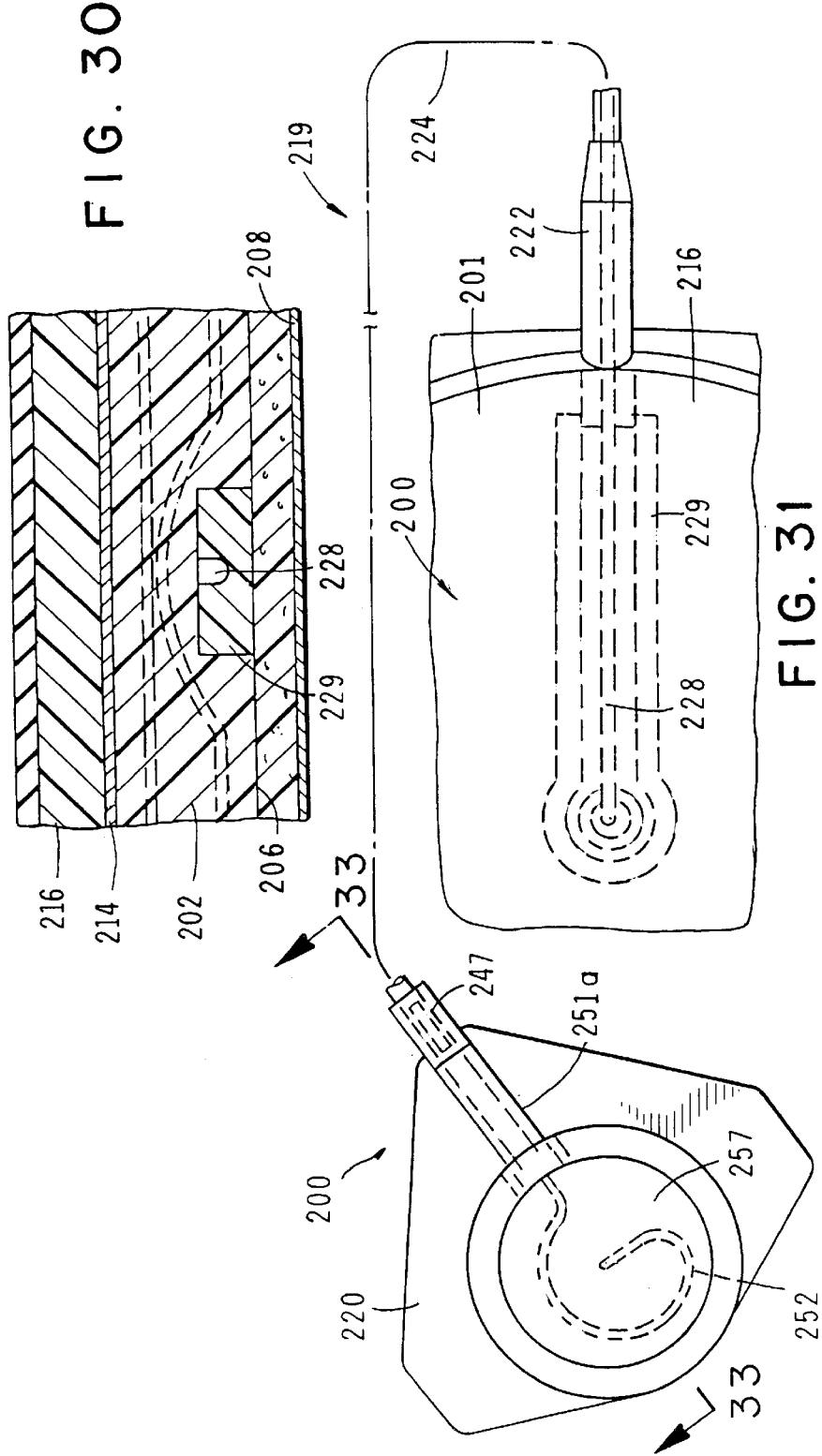

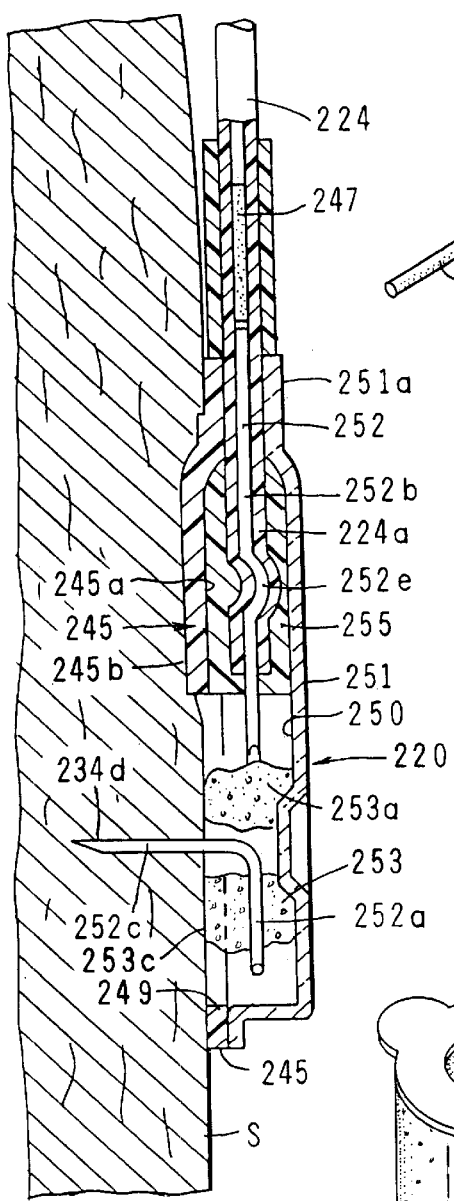
FIG. 33
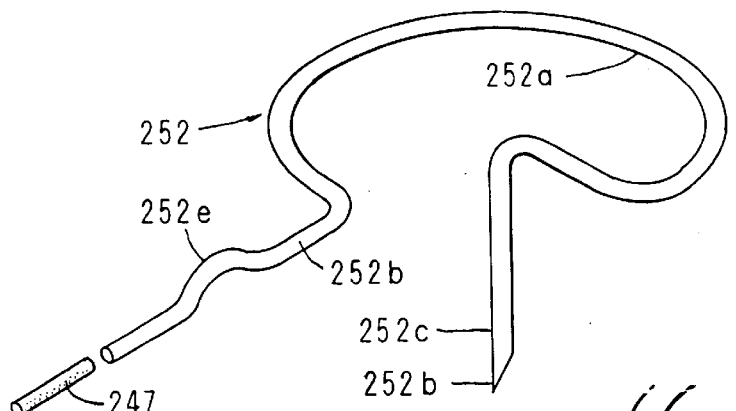
FIG. 34
FIG. 34A
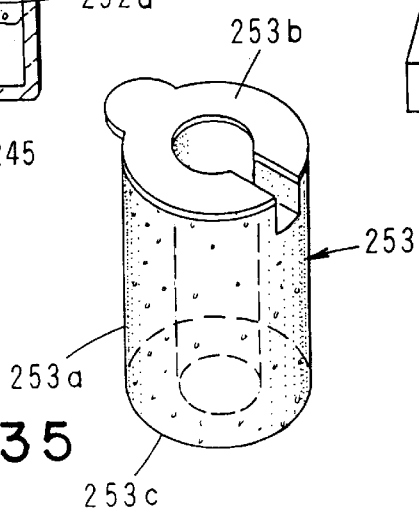
FIG. 35
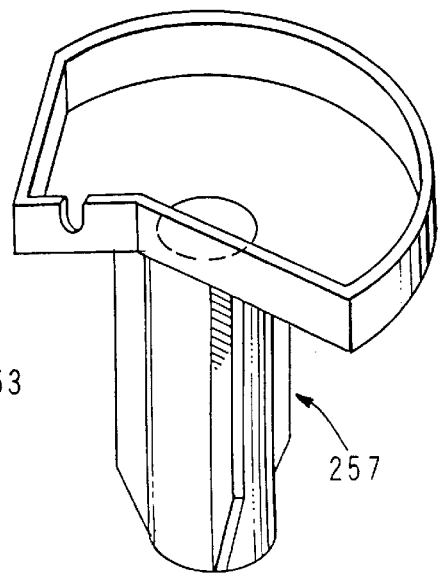
FIG. 36

FLUID DELIVERY DEVICE WITH COLLAPSIBLE NEEDLE COVER

BACKGROUND OF THE INVENTION

1. Field of The Invention

The present invention relates generally to fluid delivery devices. More particularly, the invention concerns an improved fluid delivery apparatus for precise subdermal delivery over time of medicinal liquids to an ambulatory patient, the device including a unique collapsible needle cover and a novel septum anti-invasion feature.

2. Discussion of The Prior Art

A number of different types of liquid dispensers for dispensing medicaments to ambulatory patients have been suggested. Many of the devices seek either to improve or to replace the traditional hypodermic syringe which has been the standard for delivery of liquid medicaments such as insulin solution or other beneficial agents such as hormones, peptides, and biologically active agents.

Those patients that require frequent injections of the same or different amounts of medicament, find the use of the hypodermic syringe both inconvenient and unpleasant. Further, for each injection, it is necessary to first draw the injection dose into the syringe, then check the dose and, after making certain that all air has been expelled from the syringe, finally, inject the dose. This cumbersome and tedious procedure creates an unacceptable probability of debilitating complications, particularly for the elderly and the infirm. Further, the act of inserting a needle into the skin is a practice some new patients, especially pediatric patients, may find traumatic thus adding to the discomfort they may experience during therapy.

One example of the urgent need for an improved liquid delivery device for ambulatory patients can be found in the stringent therapeutic regimens used by insulin-dependent diabetics. The therapeutic objective for diabetics is to consistently maintain blood glucose levels within a normal range much as the normally functioning pancreas would do by secreting a very low level of extremely fast-acting insulin at a basal rate into the blood stream throughout the day and night.

Consider the normal individual who doesn't have diabetes, this individual's cells require energy throughout the day just to maintain a basal metabolic rate. This energy is supplied to the cells by glucose that is transported from the bloodstream to the cells by insulin. When food is consumed, the blood glucose level rises and the pancreas responds by releasing a surge of fast-acting insulin. To mimic this natural process with individual injections, the patient would have to continuously administer minuscule amounts of fast-acting insulin every few minutes throughout the day and night.

Conventional therapy usually involves injecting, separately, or in combination, fast-acting and slower-acting insulin by syringe several times a day. The dose must be calculated based on glucose levels present in the blood. Slower-acting insulin is usually administered in the morning and evening to take advantage of longer periods of lower level glucose uptake. Fast-acting insulin is usually injected prior to meals. If the dosage of fast-acting insulin is off, the bolus administered may lead to acute levels of either glucose or insulin resulting in complications, including unconsciousness or coma. Over time, high concentrations of glucose in the blood together with the absence of hormone insulin can also lead to a variety of chronic health problems, such as vision loss, kidney failure, heart disease, nerve damage, and amputations.

A recently completed study entitled The Diabetes Control and Complications Trial (DCCT) sponsored by the National Institutes of Health (NIH) investigated the effects of different therapeutic regimens on the health outcomes of insulin-dependent diabetics. This study revealed some distinct advantages in the adoption of certain therapeutic regimens. Intensive therapy that involved intensive blood glucose monitoring and more frequent, multiple injections of insulin by conventional means, for example, syringes, throughout the day saw dramatic decreases in the incidence of debilitating complications.

The NIH study also raises the question of practicality and patient adherence to an intensive therapy regimen. A bona fide improvement in insulin therapy management must focus on the facilitation of patient comfort and convenience as well as dosage and administration schemes. Basal rate delivery of insulin or other diabetes related therapeutic agents by means of a convenient and reliable delivery device over an extended period of time represents one means of improving diabetes management. Basal rate delivery involves the delivery of very small volumes of fluid (for example, 0.3–3 mL. depending on body mass) over comparatively long periods of time (18–24) hours). As will be appreciated from the discussion which follows, the apparatus of the present invention is uniquely suited to provide precise fluid delivery management at a low cost in those cases where a variety of precise dosage schemes are of utmost importance.

An additional important feature of the apparatus of the present invention is the provision of a novel reservoir filling means disposed on the underside of the base.

Another feature of the improved apparatus of the invention comprises a novel reservoir fill adapter means for permitting the reservoir of the device to be filled by syringe-type filling means, the fill adapter being removable from the delivery device following reservoir filling.

Another feature of the improved apparatus of the invention comprises a novel septum anti-invasion means which prevents refilling of the reservoir of the device following use.

Still another important aspect of the invention is the provision of novel, collapsible needle covers of various designs which, during the injection step, crush, collapse or retract to permit insertion of the needle into the patient. These novel needle covers enable a patient to use the device without being aware of the insertion of a needle into the skin while at the same time maintaining the aseptic presentation of the cannula.

With regard to the prior art, one of the most versatile and unique fluid delivery apparatus developed in recent years is that developed by one of the present inventors and described in U.S. Pat. No. 5,205,820. The components of this novel fluid delivery apparatus generally include: a base assembly, an elastomeric membrane serving as a stored energy means, fluid flow channels for filling and delivery, flow control means, a cover, and an ullage which comprises a part of the base assembly.

Another useful liquid delivery device is that described in U.S. Pat. No. 5,514,097 issued to Knauer. The Knauer device comprises a medicament injection apparatus for subcutaneous or intramuscular delivery of a medicament which conceals the infusion needle behind a needle shroud. On apparatus activation, the needle is thrust forward, pushing the needle tip outside the needle shroud with enough force to puncture the skin. The needle is thus automatically introduced into the tissue at the proper needle/skin orientation. In the same action, the apparatus automatically dispenses an accurate pre-set dose.

U.S. Pat. No. 5,226,896 issued to Harris also describes a useful prior art device. This device comprises a multidose syringe having the same general appearance as a pen or mechanical pencil. The Harris device is specifically adapted to provide for multiple measured injections of materials such as insulin or human growth hormones.

Still another type of liquid delivery device is disclosed in U.S. Pat. No. 4,592,745 issued to Rex et al. This device is, in principle, constructed as a hypodermic syringe, but differs in that it enables dispensing of a predetermined portion from the available medicine and in that it dispenses very accurate doses.

The present invention seeks to significantly improve over the prior art by providing a novel fluid delivery device having unique filling and delivery means for filling the fluid reservoir of the device and for safely and precisely dispensing medicinal fluids therefrom.

SUMMARY OF THE INVENTION

It is an object of the present invention to provide an apparatus having a self-contained stored energy means for expelling fluids at a precisely controlled rate which is of a compact, laminate construction. More particularly, it is an object of the invention to provide such an apparatus which is of very low profile so that it can conveniently be used for the precise delivery of pharmaceutical fluids, such as morphine, insulin solution and the like, into an ambulatory patient at controlled rates over extended periods of time.

It is another object of the invention to provide an apparatus of the aforementioned character which is highly reliable and very easy-to-use by lay persons in a non-hospital environment.

Another object of the invention is to provide an apparatus of the character described in the preceding paragraphs which includes novel reservoir filling means for conveniently filling the fluid reservoir of the device.

Another object of the invention is to provide an apparatus of the character described which includes a novel fill adapter which permits filing of the reservoir of the apparatus with a syringe of conventional construction.

Another object of the invention is to provide an apparatus as described in the preceding paragraph in which the fill adapter is mounted either on the side of the device base or alternatively on the bottom of the base and can be readily broken away from the base in a manner to substantially close the cannula access opening following the reservoir filling step so as to prevent system reuse.

Another object of the invention is to provide an apparatus of the class described which further includes delivery means for precisely delivering medicinal fluids to the patient including the provision of novel, crushable, collapsible or retractable needle covers of various design which surrounds and protects the infusion cannula until time of use and then readily deforms and retracts into a noninterference position as the device is connected to the patient so as to permit the needle to cleanly penetrate the patient's skin.

Another object of the invention is to provide a novel fail-safe, two-stage flow control means which in one form of the invention includes first and second flow control elements which provide redundant reliability.

Another object of the invention is to provide an apparatus of the class described which further includes cover means for the delivery means which maintains the delivery means in an aseptic condition and provides for a practical means of self-administration by patients (such as young patients or needle adverse patients) which does not require their conscious observation of needle insertion.

Another object of the invention is to provide an apparatus of the character described which, due to its unique construction, can be manufactured inexpensively in large volume by automated machinery.

Other objects of the invention are set forth in the co-pending United States applications which are incorporated herein by reference and still further objects will become apparent from the discussion which follows.

BRIEF DESCRIPTION OF THE DRAWINGS

FIG. 1 is a generally perspective view of one form of the fluid delivery device of the present invention.

FIG. 1A is an enlarged, cross-sectional view taken along lines 1A—1A of FIG. 1 showing the reservoir fill adapter of the invention connected to the base of the device and the delivery cannula surrounded by one form of the crushable needle cover of the invention.

FIG. 2 is an enlarged, generally perspective view of the crushable needle cover of the device shown in FIG. 1A.

FIG. 3 is a greatly enlarged, fragmentary, cross-sectional view of a portion of the base and of the reservoir fill adapter of the invention.

FIG. 4 is a cross-sectional view similar to FIG. 3 but showing the filling syringe of the apparatus interconnected with the downwardly extending fill adapter of the device.

FIG. 5 is a cross-sectional view similar to FIG. 3 but illustrating the breaking away of the fill adapter following the reservoir filling step.

FIG. 6 is an enlarged, cross-sectional view of one form of the filling syringe of the invention.

FIG. 7 is a cross-sectional view of the device as it appears immediately prior to its interconnection with the patient.

FIG. 8 is a cross-sectional view similar to FIG. 7, but showing the device interconnected with the patient with the needle cover in a crushed configuration.

FIG. 9 is a side-elevational, cross-sectional view of an alternate form of the invention having a different type of needle cover from that shown in FIG. 1A.

FIG. 10 is an enlarged, generally perspective view of the collapsible needle cover of the apparatus shown in FIG. 9.

FIG. 11 is a side-elevational, cross-sectional view similar to FIG. 9, but showing the device as it appears immediately prior to interconnection with the patient with the fill adapter removed and the fluid reservoir filled with the beneficial agent to be infused into the patient.

FIG. 12 is a side-elevational, cross-sectional view similar to FIG. 11 but showing the device interconnected with the patient with the bellows which surrounds the cannula in a collapsed configuration.

FIG. 15 is a side-elevational, cross-sectional view similar to FIG. 9, but showing the device as it appears immediately prior to interconnection with the patient with the fill adapter removed and the fluid reservoir filled with the beneficial agent to be infused into the patient.

FIG. 16 is a side-elevational, cross-sectional view similar to FIG. 15 but showing the device interconnected with the patient.

FIG. 18 is a side-elevational, cross-sectional similar to FIG. 17, but showing a different type of reservoir fill means interconnected with the outwardly extending fill adapter of the device shown in FIG. 17.

FIG. 20 is an enlarged, cross-sectional view taken along lines 20—20 of FIG. 17.

FIG. 24 is a cross-sectional view taken along lines 24—24 of FIG. 19.

FIG. 25 is a foreshortened, side-elevational view of the reservoir filling means of the apparatus as it appears after being broken away from the side mounted fill adapter.

FIG. 26 is a side-elevational, cross-sectional view of the delivery device of FIG. 17 affixed to the patient.

FIG. 26A is an enlarged, fragmentary, cross-sectional view of the area of FIG. 26 designated as 26A.

FIG. 27 is a cross-sectional view of still another form of fluid delivery device of the invention which includes an alternate type of infusion means.

FIG. 27A is a greatly enlarged, cross-sectional view of one of the fluid flow control means of the apparatus shown in FIG. 27.

FIG. 28 is a cross-sectional view taken along lines 28—28 of FIG. 27.

FIG. 29 is a greatly enlarged, cross-sectional view of the area of FIG. 27 identified by the numeral 29.

FIG. 30 is a cross-sectional view taken along lines 30—30 of FIG. 27.

FIG. 31 is a fragmentary top plan view of the infusion means of this latest form of the invention.

FIG. 32 is a fragmentary top plan view of a portion of the flow control element of the infusion means shown in FIG. 31.

FIG. 33 is a cross-sectional view taken along lines 33—33 of FIG. 31 showing the infusion means connected to the patient.

FIG. 34 is a generally perspective view of the infusion cannula of the apparatus shown in FIG. 31.

FIG. 34A is a fragmentary, generally perspective view of an alternate form of cannula and flow control means wherein the flow control means is disposed within a collar formed on the cannula.

FIG. 35 is an enlarged, generally perspective view of the collapsible needle cover of the infusion means of this latest form of the invention.

FIG. 36 is an enlarged, generally perspective view of the protective sheath of the embodiment shown in FIG. 31 which covers the collapsible needle cover of the infusion means.

DESCRIPTION OF THE INVENTION

Figure 13:
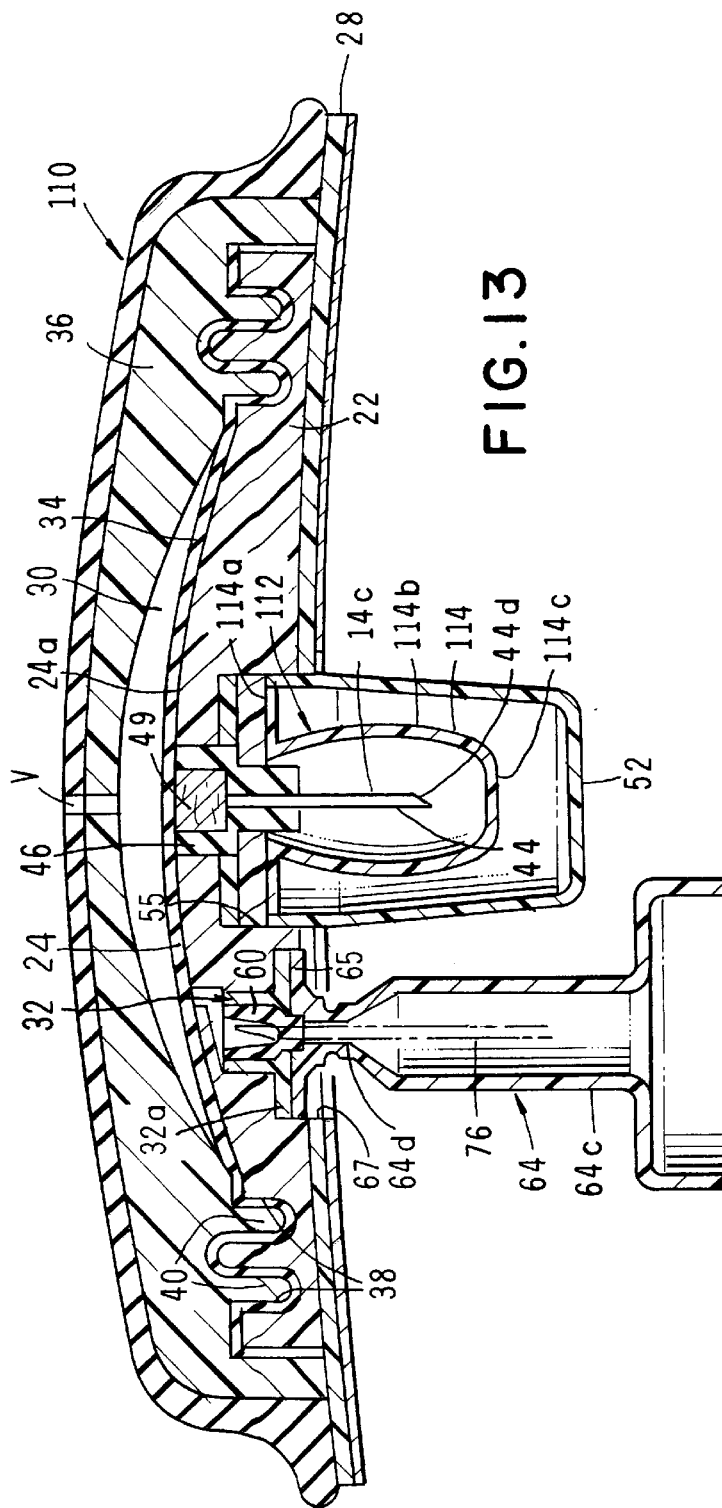
FIG. 13 is a side-elevational, cross-sectional view of still another alternate form of the invention having a different type of needle cover from that shown in FIGS. 1A and 9.

Referring to the drawings and particularly to FIGS. 1 through 8, one form of the fluid delivery device of the invention is there shown and generally designated by the numeral 20. This form of the invention, which is specially designed for subdermal infusion of selected medicaments, comprises a base 22 having an upper surface 24 including a generally dome shaped central portion 24a and a peripheral portion 24b circumscribing central portion 24a. As best seen in FIG. 1A, base 22 is also provided with a lower surface 26 to which a patient interconnection means or adhesive pad assembly 28 is connected. Pad assembly 28, which comprises a foam pad 28a having adhesive on both sides, functions to releasably interconnect the device to the patient so as to hold it securely in place during the medicament delivery step. A peal-away member 28b covers the lower surface of the pad 28a.

A stored energy means cooperates with the upper surface 24 of base 22 to form a reservoir 30 (FIG. 7) having an inlet port assembly 32 (FIGS. 3 and 4), which, in a manner presently to be described, is adapted to cooperate with a filling means for filling reservoir 30 with the medicinal fluid to be infused into the patient. The stored energy means is here provided in the form of at least one distendable membrane 34 which is superimposed over base 22. Membrane 34 is distendable as a result of pressure imparted on the membrane by fluids introduced into reservoir 30 via inlet port assembly 32 (FIGS. 3 and 4). As membrane 34 is distended in the manner shown in FIG. 7, internal stresses will be established, which stresses tend to move the membrane toward a less distended configuration and in a direction toward upper surface 24 of base 22. Membrane 34 can be constructed from a single membrane or from multiple membranes which are overlayed to form a laminate construction or alternatively form a coated single membrane.

Provided within the reservoir of the device, which is defined by the upper surface 24a of the base and a concave surface 36a of a cover means for covering the distendable membrane, is ullage defining means for providing ullage within the reservoir and for engagement with membrane 34 as the membrane moves toward its less distended starting configuration. The ullage defining means here comprises the previously identified, dome shaped central portion 24a of base 22. When the distendable membrane after being distended, tends to return toward its less distended configuration, fluid contained within the reservoir 30 will flow uniformly outwardly of the reservoir through the infusion means of the invention for infusing the medicinal fluids contained within the reservoir into the patient.

Superimposed over base 22 is the cover means, shown here as a rigid cover 36 which functions, through the use of novel sealing means, to sealably enclose membrane 34. The sealing means here comprises a pair of generally circular grooves 38 formed in peripheral surface 24b of base 22 and a pair of cooperating, generally circular shaped rim like protuberances 40 formed on the peripheral lower surface 36b of the cover 36. Protuberances 40 are receivable within grooves 38 in the manner shown in FIG. 1A and function to sealably clamp distendable membrane 34 between the cover and the base. Cover 36 includes a vent aperture "V" for venting any gases that may be trapped between membrane 34 and the concave interior surface of cover 36.

Examples of materials found particularly well suited for the construction of distendable membrane 34 include: silicone polymers (polysiloxanes) (high performance silicone elastomers made from high molecular weight polymers with appropriate fillers added). These materials are castable into thin film membranes and have high permeability (which allows maximum transport of vapor and gas), high bond and tear strength and excellent low temperature flexibility and radiation resistance. Additionally, silicone elastomers retain their properties over a wide range of temperatures (−80° to 200° C.) are stable at high temperatures, and exhibit tensile strengths up to 2,000 lb./in$^2$ elongation up to 600%. Another suitable material for the stored energy membrane is natural and synthetic latex.

Manufacturers of materials suitable for use in construction of the distendable membrane include Dow Chemical, General Electric, B.P. Polymers, Mobay Chemical, Shell Oil Corp., Petrarch Systems, DuPont, Concept Polymers, Goodyear and Union Carbide Corp.

With respect to the structural cover 36 and base 22, these components can also be produced from a variety of materials including one of several polymer groups. The degree of hardness of these materials can range from soft, resilient or rigid, and the following polymers can be employed: Polypropylene (PP), Ultra high molecular weight polyethylene (UHMW PE), High density polyethylene (HDPE), Polyvinylidene Fluoride (PVDF), Ethylenevinyl acetate (EVA), Styrene Acrylonitrile (SAN), Polytetrafluoroethylene (PTFF). A suitable source of these materials is Porex Technologies of Fairburn, Ga. It is to be understood that other suitable materials well known to those skilled in the art can also be used, including a material sold by B.P. Chemicals International of Cleveland, Ohio, under the name and style "Barex". This material is a clear rubber modified Acrylonitrile Copolymer which has wide application in the packaging industry because of its superior gas barrier, chemical resistance and extrusion (thermoforming) and injection molding capabilities.

Other suitable materials for the construction of the various components of the device of the present invention are described in U.S. Pat. No. 5,205,820 which issued to one of the present inventors. This patent is hereby incorporated by reference as though fully set forth herein.

Referring particularly to FIG. 1A, the infusion means of this latest form of the invention for subdermal infusion of medicaments into the patient, can be seen to include, a downwardly extending hollow cannula 44 which is carried by a support member 46 that is received within a cavity 48 formed in base 22. Support member 46 also functions to support, within a cavity 47, flow control means for controlling the rate of fluid flow from reservoir 30 toward hollow cannula 44. This flow control means is here provided as a porous rate control frit 49 which can be constructed from a micro porous metal such as stainless steel. The frit can also be constructed from a porous ceramic or porous plastic material. Rather than using a porous frit, the rate control means can take the form of an assembly of the character shown in FIG. 27A which comprises a filter element and a novel wafer-like element having a laser drilled microbore. The details of this alternate type of flow control means will be described in greater detail hereinafter.

Hollow cannula 44 has an inlet end 44a and an outlet end 44d formed in a needle-like segment 44c which extends generally perpendicularly downward from the lower surface 26 of base 22 (FIG. 8) and terminates in a piercing point 44d. To protect the hollow cannula and its crushable cover 50 from damage, a removable protective cover assembly 52 surrounds cannula 44 and cover 50. Cover assembly 52 includes a downwardly depending sheath portion 52a, the upper end of which is closely receivable within a cavity 55 formed in base 22. At time of use the cover assembly 52 can be removed from the cavity 55 as shown in FIG. 7 to expose the crushable cover 50 the details of construction of which will presently be described.

Referring once again to FIGS. 1A, 3, and 4, one form of the novel filling means of the present invention is there illustrated. As previously mentioned, the filling means functions to controllably fill reservoir 30 with the medicinal fluid which is to be infused into the patient. In the present form of the invention, the filling means comprises a septum 60, a filling syringe assembly and a novel fill adapter assembly. As best seen in FIG. 3, septum 60, which comprises a pierceable elastomer, is sealably disposed within the previously mentioned fill port assembly 32 which is connected to base 22.

As shown in FIGS. 3 and 4, fill port assembly 32 includes a base portion 32a which engages the fill adapter 64 of the invention when the fill adapter is connected to base 22 in the manner shown in FIGS. 1A, 3 and 4. In this regard, fill adapter 64 includes a flange 65, which engages the fill port assembly 32. Adapter 64 also includes a lower, generally cylindrical wall portion 64b and a generally cylindrical intermediate wall portion 64c. As best seen in FIG. 3, the upper extremity of wall portion 64c is necked down to define a small cannula receiving opening 64d and flange 65 of the adapter is receivable within a cavity 67 formed in base 22 so that the adapter can be joined to the base.

Also forming a part of the filling means of the present invention is a filling syringe assembly 68 which, as best seen in FIG. 6, includes a vial like container 70 having a fluid reservoir 70a, a needle housing 72 closing fluid reservoir 70a, and a double ended piercing needle 76 carried by needle housing 72. Filling syringe assembly 68 also includes an elongated housing assembly 78 which houses medicament vial 70. Housing assembly 78 is made up of a hollow housing 78a and a spacer sleeve 78b which insures a close fit of vial 70 within hollow housing 78a. As shown in FIGS. 4 and 6, the fluid reservoir 70a of vial 70 is sealed at one end by a pierceable closure septum 80 and is sealed proximate its opposite end by an elastomeric plunger 82 (FIG. 6) which is telescopically movable along the length of reservoir 70a to expel fluid therefrom via needle 76. The needle housing 72, which supports needle 76 includes an internally threaded collar 72b which enables threadable interconnection of the needle housing with hollow housing 78a in the manner shown in FIG. 6 so that the inwardly extending portion 76a of the needle will pierce closure septum 80 upon interconnection of the needle housing with hollow housing 78a. With this construction, portion 76b of needle 76 extends forwardly to enable the needle to pierce septum 60 upon mating the syringe assembly with adapter 64 in the manner shown in FIG. 4.

In using filling syringe assembly 68 to fill reservoir 30 of the delivery portion of the device, a protective cover 83 is first pulled away from the bottom of adapter 64 (FIG. 1A) and protective cap 85 is removed from the syringe assembly (FIG. 6). Next, needle housing 72 along with needle 76 are telescopically inserted into adapter 64 in the manner shown in FIG. 4 so that the boss 73 of needle housing 72 is closely received within the lower part of intermediate portion 64c.

Also forming an important part of the filling syringe assembly 68 of the present form of the invention, is a pusher sleeve 88 which is telescopically receivable over housing 78 in the manner shown in FIG. 6. Disposed internally of sleeve 88 is a pusher rod 90 which is adapted to engage plunger 82 and move it longitudinally of reservoir 70a as the pusher sleeve is moved from a first extended position to a position wherein a substantial portion of housing 78 is encapsulated within the sleeve. As sleeve 88 is moved toward the second position, plunger 82 will move inwardly of reservoir 70a causing fluid contained therein to flow toward reservoir 30 of the delivery device via hollow needle 76 (see FIG. 4).

Turning particularly to FIGS. 3 and 4, it is to be noted that cylindrical body section 64c of adapter 64 is provided with a serration 64e which permits body section 64c to be easily separated from flange 65 by a twisting motion in the manner shown in FIG. 5. As the adapter 64 is twisted relative to base 22, the upper necked down area of wall portion 64c will deform in a manner to substantially close cannula receiving opening 64d so that the reservoir of the device cannot be refilled. To insure substantial closing of opening 64d in the manner shown, as for example, in FIGS. 5, 11 and 15, a suitable polymer is preferably used to form the adapter. Examples of suitable materials for this purpose include silicon, vinyl and polypropylene. It is to be understood that, although the fill adapter is shown interconnected with the lower surface of the base of the device, it could also be connected to the side surfaces or to any other convenient surface.

In using the apparatus of the form of the invention shown in FIGS. 1 through 8, following filling of reservoir 30, portions 64b and 64c of the fill adapter are separated from flange 65 by twisting the adapter in the manner described in the preceding paragraph which results in the substantial closing of cannula receiving aperture 64d (FIG. 5). This done, cover assembly 52 is removed from cavity 55 and peel away member 28b is removed so that the device is in condition for interconnection with the patient. This is accomplished by pressing the base 50a of crushable cover 50 against the patient's skin "S" (see FIG. 7). A downward force exerted against cover 36 will cause crushable cover 50 to crush in the manner shown in FIG. 8 allowing the needle portion 44d of the cannula to penetrate the patient's skin and tissue in the manner shown in FIG. 8. This unique construction of the needle cover enables the patient to use the device without being aware of the insertion of the needle into the skin while at the same time maintaining the needle in a substantially aseptic condition. As the base of the device is painlessly moved into contact with the patient, adhesive pad 28 will grip the patient's skin so as to hold the device securely in position. The highly novel crushable cover 50, can be constructed from various materials including a low-density, open cell foam such as a hydrophilic polyurethane product sold by Hampshire Chemical Corporation of Lexington, Mass. under the name and style HYPOL. This material, as well as similar foam materials used for the construction of cover 50, is non-resilient so that, after being crushed, it will remain in the configuration shown in FIG. 8 and thereby will not interfere with the positioning of the base against the patient's skin. Cover 50 could also be constructed from a low density hydrophobic foam, such as polyisoprene, from a soft polymer gel or a hydrophobic gel that is swollen with mineral oil and from like materials. Cover 50 preferably includes an adhesive coated upper surface 50c which functions to affix the cover to a potting material 51 which surrounds the neck 46a of support member 46. To protect surface 50c prior to assembly, a peel away cover 50b is provided (see FIG. 2).

Turning next to FIGS. 9 through 12, an alternate form of the invention is there shown. This alternate embodiment is similar in many respects to that shown in FIGS. 1 through 8 and like numerals are used to identify like components. The major difference between this latest embodiment and that shown in FIGS. 1 through 8, concerns the infusion means for subdermal infusion of medicaments into the patient. As before, this infusion means includes a downwardly extending hollow cannula 44 which is carried by a support member 46 that is received within a cavity 55 formed in base 22. As before, support member 46 functions to support flow control means of the character previously described for controlling the rate of fluid flow from reservoir 30 toward hollow cannula 44. However, rather than the cannula cover comprising a crushable material, as in the first embodiment of the invention, the cover is here provided as a uniquely configured, yieldably deformable collapsible bellows assembly 102.

Bellows assembly 102 surrounds cannula 44 in the manner shown in FIG. 9 and is movable from the extended position shown in FIG. 9 to the collapsed position shown in FIG. 12. As best seen in FIG. 10, bellows assembly 102 includes a bellows-like body 104 having an adhesive coated upper surface 104a (FIG. 10) and a collapsible sidewall 104b. Prior to interconnecting the bellows 104 to base 22, surface 104a is protected by a peel-away cover 106. Body 104 can be constructed of various yieldably deformable materials such as a silicone elastomer, a latex rubber, a thermoplastic elastomer, a thermoplastic polyurethane, a polyolefin thermoplastic elastomer and like materials. Suitable materials for constructing body 104 are readily commercially available from sources such as J. P. Stevens, Exxon and duPont-Dow.

In using the apparatus of the embodiment shown in FIGS. 9 through 12, following filling of reservoir 30, portions 64b and 64c of the fill adapter are broken away from the flange 65 along serrations 64e (see FIG. 5). This done, cover assembly 52 is removed from cavity 55 and peel away member 28b is stripped away so that the device is placed in condition for interconnection with the patient. This is accomplished by pressing the base 104c of bellows body 104 against the patient's skin "S" (see FIG. 11). A downward force exerted against cover 36 will cause bellows body 104 to collapse in the manner shown in FIG. 12 allowing the needle portion 44d of the cannula to first penetrate and pass through base 104c and then to enter the patient's skin and tissue in the manner shown in FIG. 12. As the base of the device is moved into contact with the patient, adhesive pad 28 will grip the patient's skin so as to hold the device securely in position with the cannula appropriately implanted in a subdermal or introdermal position.

Figure 14:
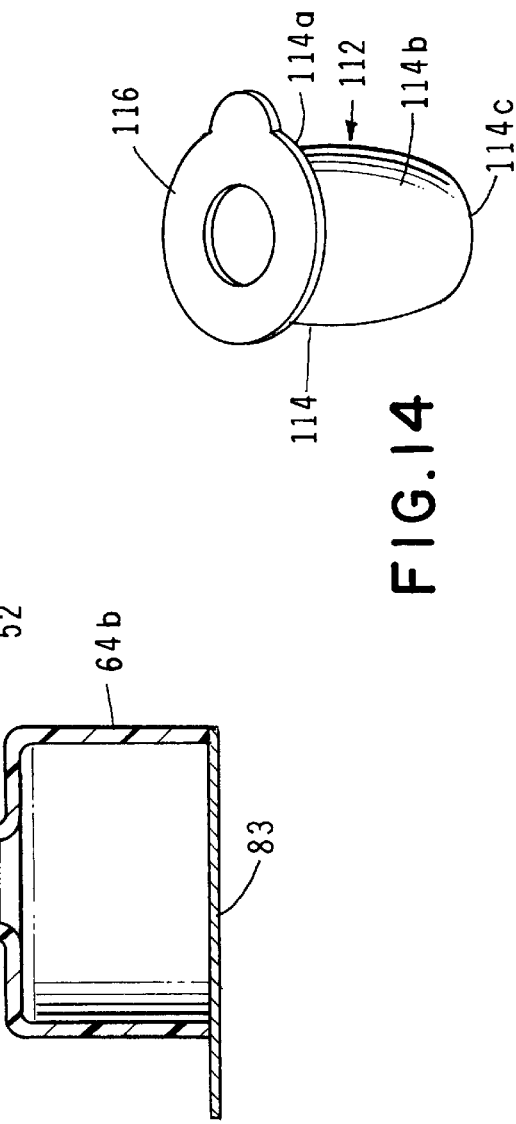
FIG. 14 is an enlarged, generally perspective view of the collapsible needle cover of the apparatus shown in FIG. 13.

Turning next to FIGS. 13 through 16, still another form of the invention is there shown and generally identified by the numeral 110. This alternate form is also similar in many respects to that shown in FIGS. 1 through 12 and like numerals are used to identify like components. The major difference between this latest embodiment and that shown in FIGS. 1 through 12, once again concerns the infusion means for subdermal infusion of medicaments into the patient. As before, the infusion means includes a downwardly extending hollow cannula 44 which is carried by a support member 46 that is received within a cavity 55 formed in base 22. Support member 46 also functions to support flow control means of the character previously described for controlling the rate of fluid flow from reservoir 30 toward hollow cannula 44. However, rather than the cannula cover comprising a crushable material, or a collapsible and retractable bellows as was the case in the first and second embodiments of the invention, the cover is here provided in the form of a yieldably deformable balloon-like member 112 (FIG. 14).

Balloon-like member 112 surrounds cannula 44 in the manner shown in FIG. 13 and is yieldably deformable from the position shown in FIG. 13 to the collapsed position shown in FIG. 16. As in the earlier described needle cover assemblies, member 112 includes a body 114 having an adhesive coated upper surface 114a (FIG. 13) and a yieldably deformable sidewall 114b. Prior to interconnecting member 112 to base 22, surface 114a is protected by a peel-away cover 116. Member 112 can be constructed from various yieldably deformable materials, including the materials used to construct the collapsible bellows 104.

In using the apparatus of the embodiment shown in FIGS. 13 through 16, following filling of reservoir 30, portions 64b and 64c of the fill adapter are once again broken away and cover assembly 52 is removed from the base to place the device in condition for interconnection with the patient. This is accomplished by pressing the lower surface of body 114c against the patient's skin "S" (see FIG. 15). A downward force exerted against cover 36 will cause member 112 to deform in the manner shown in FIG. 16 allowing the needle portion 44d of the cannula to first penetrate and pass through the base 114c of the needle cover and then to penetrate the patient's skin and tissue in the manner shown in FIG. 16. As before, the novel needle cover maintains the needle in a substantially sterile and aseptic condition and psychologically aids the patient in the needle insertion step.

Turning next to FIGS. 17 through 26, yet another form of the fluid delivery apparatus of the invention is there shown and generally designated by the numeral 120 (FIG. 18). This form of the invention, which is also designed for subdermal infusion of selected medicaments, comprises a base 122 having an upper surface 124, including a generally dome shaped central portion 124a and a peripheral portion 124b circumscribing central portion 124a. As before, base 122 is provided with a lower surface 126 to which a patient interconnection means or adhesive pad assembly 128 is connected. Pad assembly 128, which is of similar construction to pad assembly 28, functions to releasably interconnect the device to the patient so as to hold it securely in place during the medicament delivery step.

A stored energy means cooperates with the upper surface 124 of base 122 to form a reservoir 130 (FIG. 18) having an inlet. An inlet port assembly 132 is provided in peripheral portion 124b and in a manner presently to be described, is adapted to cooperate with a reservoir filling means of slightly different construction for filling reservoir 130 with the medicinal fluid to be infused into the patient (see FIGS. 17 and 18). The stored energy means is here provided in the form of a distendable membrane 134 which is superimposed over base 122. Membrane 134 is distendable as a result of pressure imparted on the membrane by fluids introduced into reservoir 130 via inlet 132a of inlet port assembly 132 (FIG. 18). As membrane 134 is distended in the manner shown in FIG. 18, internal stresses will be established, which stresses tend to urge the membrane toward a less distended configuration and in a direction toward upper surface 124a of base 122.

Provided within the reservoir of the device, which is defined by the upper surface 124a of the base and a concave surface 136a of a cover means for covering the distendable membrane, is ullage defining means for providing ullage within the reservoir and for engagement with membrane 134 as the membrane moves toward its less distended starting configuration. The ullage defining means here comprises the previously identified, dome shaped central portion 124a of base 122. When the distendable membrane after being distended, tends to return toward its less distended configuration, fluid contained within the reservoir 130 will flow uniformly outwardly of the reservoir through the infusion means of the invention for infusing the medicinal fluids contained within the reservoir into the patient.

Superimposed over base 122 is the cover means, shown here as a vented rigid cover 136 which functions, through the use of novel capture means, to retain and sealably enclose membrane 134. The sealing means is of the character described in connection with the embodiment shown in FIGS. 1 through 8 and operates in precisely the same way to sealably clamp distendable membrane 134 between the cover and the base. The same materials previously discussed for constructing the cover, the base and the distendable membrane can be used to construct the components of this latest form of the invention.

Figure 17:
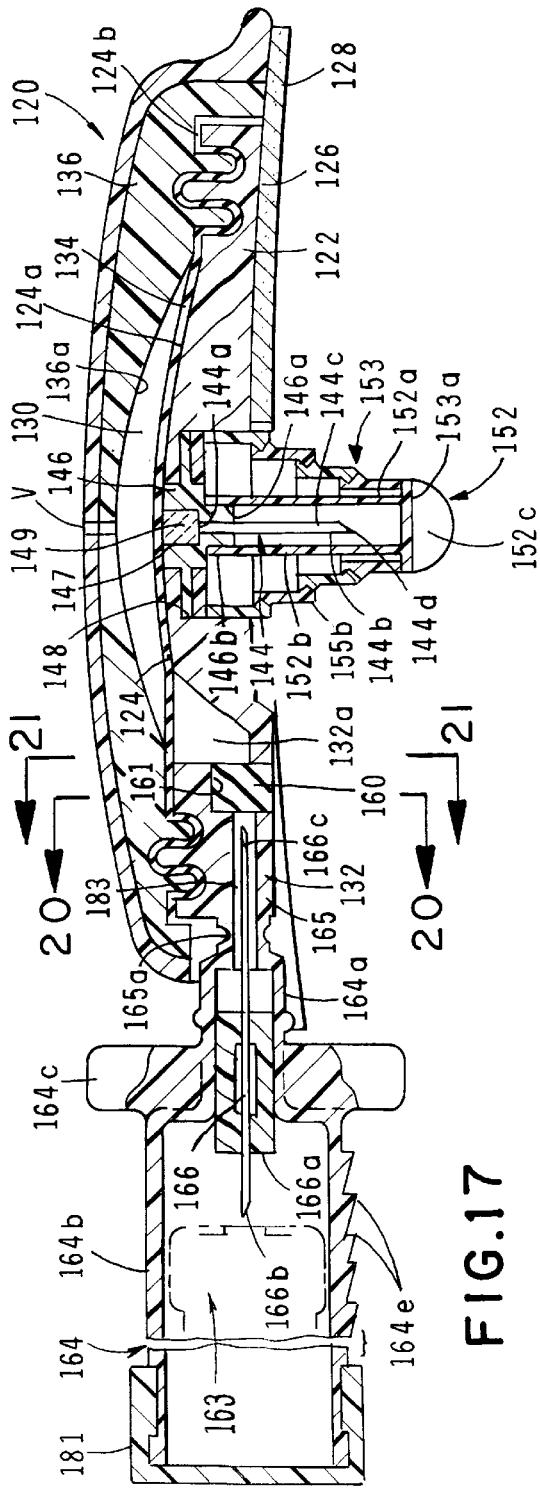
FIG. 17 is a side-elevational, cross-sectional view of a portion of yet another form of the fluid delivery device of the present invention in which the reservoir fill adapter is mounted on the side of the base component.
Figure 22:
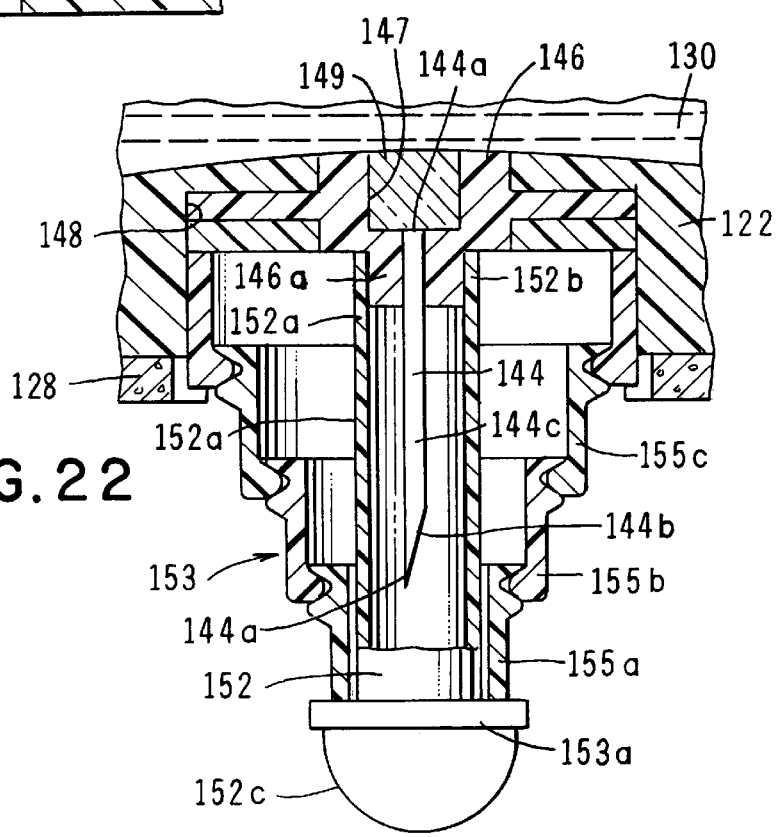
FIG. 22 is an enlarged, cross-sectional view of the area designated as 22 in FIG. 18.
Figure 23:
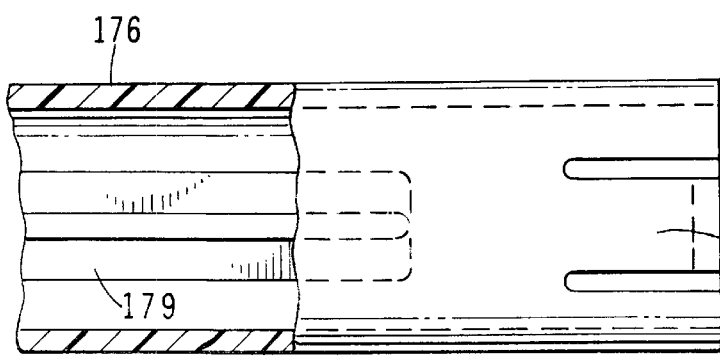
FIG. 23 is an enlarged view taken along lines 23—23 of FIG. 19.

Referring particularly to FIGS. 17, 18, and 22, the infusion means of this latest form of the invention for subdermal infusion of medicaments into the patient, can be seen to include, a downwardly extending hollow cannula 144 which is carried by a support member 146 that is received within a cavity 148 formed in base 122. Support member 146 also functions to support, within a cavity 147, flow control means for controlling the rate of fluid flow from reservoir 130 toward hollow cannula 144. This flow control means is here provided as a porous rate control frit 149 which is of the same character as the previously described rate control frit 49 (FIGS. 1A, 7, 9, 11 and 12). As previously mentioned, the flow control means can also be of the character shown in FIG. 27A.

As best seen in FIG. 22, hollow cannula 144 has an inlet end 144a and an outlet end 144b formed in a needle-like segment 144c which extends generally perpendicularly downward from the lower surface 126 of base 122 (FIG. 26) and terminates in a piercing point 144d. To protect the hollow cannula from damage, a protective cover assembly 152 surrounds cannula 144 in the manner shown in FIGS. 17 and 22. Cover assembly 152 includes a downwardly depending generally cylindrically shaped portion 152a and an upper end 152b which is closely receivable over a boss 146a formed on support 146. At time of use the cover assembly 152 can be removed from boss 146a to expose cannula 144 by gripping finger gripping means here provided as a tab 152c formed on a cover 152 which closes the outboard end of cylindrical portion 152a. Once cover assembly 152 is removed, cannula 144 is surrounded by telescoping cover 153, the character of which will presently be described.

Referring once again to FIGS. 17 and 18, the novel filling means of this latest form of the invention is there illustrated. As before, the filling means functions to controllably fill reservoir 130 with the medicinal fluid which is to be infused into the patient. In the present form of the invention, the filling means comprises a septum 160 which is mounted within a cavity 161 formed in peripheral portion 124b of base 122; a vial type fill assembly 163 (FIG. 18) and a novel fill adapter assembly 164. In this latest embodiment of the invention, the fill adapter assembly 164 is integrally formed with and extends outwardly from the side of base 122 in the manner shown in FIGS. 17 and 18. In this regard, it is to be noted that fill adapter 164 includes a generally cylindrical, reduced diameter neck portion 164a, which cooperates with base 122 to define the fill port 132 of the device and an enlarged diameter, hollow body portion 164b connected to reduced diameter portion 164a (FIG. 17). Forming a part of portion 164a is a central, twist-off segment 165 which is provided with a serration 165a, the purpose of which will presently be described. Adapter assembly 164 also includes a pair of twist-off wings 164c, for use in separating adapter assembly 164 from base 122. Slidably disposed within neck portion 164a is a needle holder 166a which supports a double ended piercing cannula 166.

Figure 19:
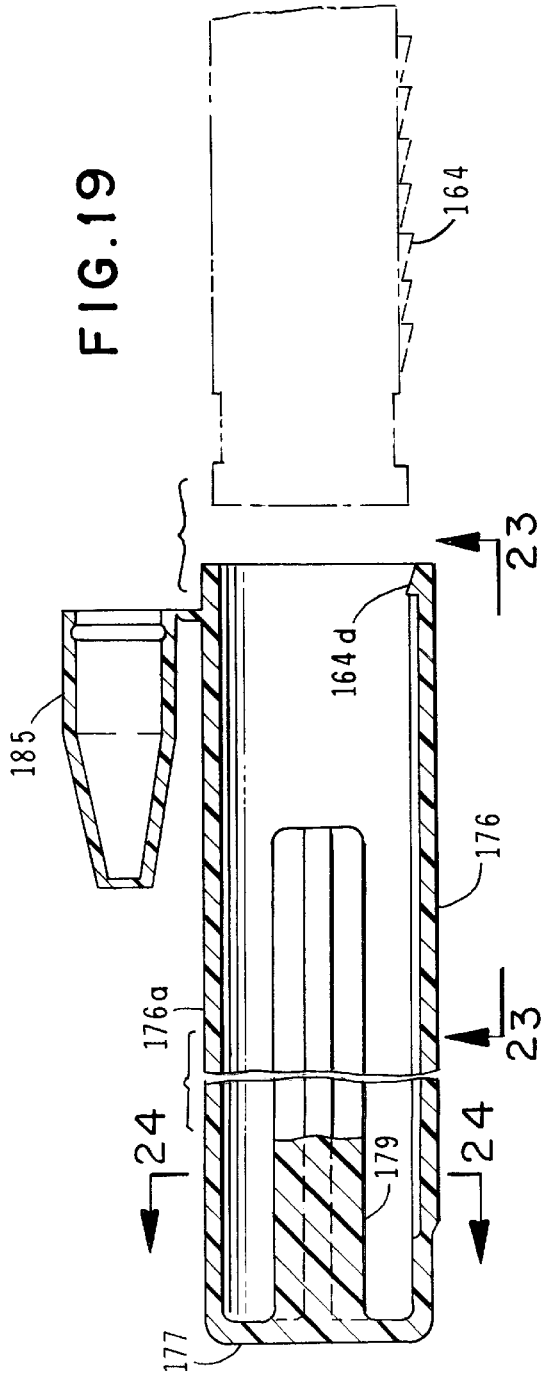
FIG. 19 is a cross-sectional view of the pusher sleeve assembly of the reservoir fill means shown in FIG. 18.
Figure 21:
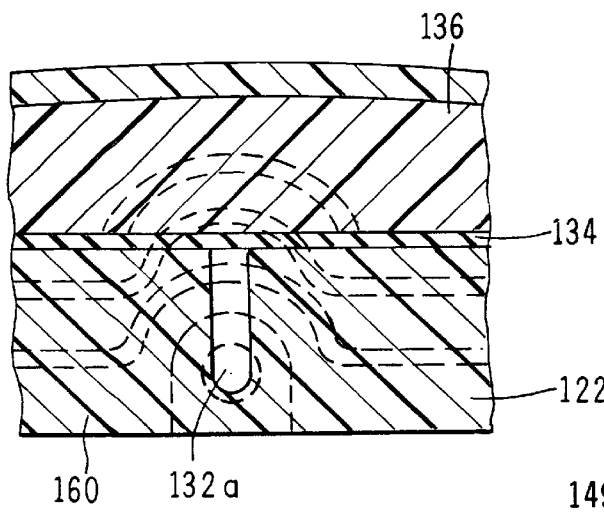
FIG. 21 is an enlarged, cross-sectional view taken along lines 21—21 of FIG. 17.

Also forming a part of the filling means of this latest form of the invention is a filling assembly which comprises the previously mentioned vial type fill assembly 163. As best seen in FIGS. 17, 18 and 19, fill assembly 163 includes a vial-like container 170 having a container reservoir 170a and a pierceable septum 172 closing one end of fluid reservoir 170a. Closing the opposite end of reservoir 170a is a telescopically movable plunger 174. Plunger 174 is telescopically movable longitudinally of reservoir 170a by a pusher sleeve assembly 176 which also forms a part of the filling means. Referring to FIG. 19, it can be seen that pusher sleeve assembly 176 comprises a hollow housing 176a which is open at one end to telescopically receive vial 170 and is closed at its opposite end by a closure wall 177. Integrally formed with wall 177 and extending inwardly of housing 176a is a pusher member 179, the inboard end of which engages plunger 174 to move the plunger along the length of reservoir 170a as housing 176 is telescopically mated with body portion 164b of adapter assembly 164 (see also FIG. 24).

In using reservoir filling means of the invention to fill reservoir 130 of the delivery portion of the device, a protective cover 181 is first removed from the outboard end of adapter body 164b (FIG. 17). Next, vial-like container 170 is telescopically inserted into portion 164b of adapter body 164. This done, pusher sleeve assembly 176 is placed over adapter body 164b so that pusher rod 179 moves into engagement with plunger 174. As the pusher sleeve assembly is telescopically mated with adapter body 164b, an inward force exerted on the pusher sleeve will push vial-like container 170 forwardly so that the outboard end 166b of double ended cannula will pierce vial septum 172. Continued inward movement of the pusher sleeve will cause needle holder 166a to move from the position shown in FIG. 17 to the position shown in FIG. 18 causing the inboard end 166c of double ended cannula 166 to pierce delivery device septum 160.

The interconnection of the components in the manner described in the preceding paragraphs and as shown in FIG. 18, places reservoir 170a of the vial-like container 170 into fluid communication with device reservoir 130 so that as plunger 174 moves inwardly of the container-like vial, the fluid contained therein will be caused to flow into reservoir 130 in the manner shown in FIG. 18. As the fluid flows into the reservoir, gases trapped between membrane 134 and inner surface 136a of the cover will be vented to atmosphere via a vent "V" formed in cover 136. Locking means, here provided as a resiliently deformable locking tab 164d (FIGS. 19 and 23) formed on sleeve 176, will lockably engage one of a plurality of locking teeth 164e (FIG. 17) formed on adapter body 164b to prevent removal of sleeve 176 from adapter assembly 164.

In using the apparatus of the form of the invention shown in FIGS. 17 through 26, following filling of reservoir 130, the neck portion 164a of adapter 164 is broken away from base 122 along serration 165a by a twisting force being imposed on twist-off wings 164c. As the adapter is twisted and separated from the base, the outboard end of the needle receiving passageway 183 will deform in the manner shown in FIG. 26 so as to substantially close the passageway and effectively prevent reentry of another syringe needle. Following separation of adapter assembly 164, a closure cap 185 which is removably carried by pusher sleeve 176, (see phantom lines in FIG. 25) is broken away and inserted over end 166c of double ended cannula 166 in the manner shown by the solid lines in FIG. 25 so as to safely encapsulate the cannula.

Next, cover assembly 152 is removed from the delivery component to expose piercing cannula 144 so as to place the apparatus in condition for interconnection with the patient. This step is accomplished by pressing the base 153a of telescoping cover 153 against the patient's skin. Next, a downward force exerted against cover 136 of the delivery component will cause segments 155a, 155b, and 155c (FIG. 22) of cover 153 to telescope relative to one another in the manner illustrated in FIG. 26 allowing the needle portion 144d of the cannula to freely penetrate the patient's skin and tissue. Once again, this unique telescoping construction of the needle cover enables the patient to use the device without being consciously aware of the insertion of the needle into the skin while at the same time maintaining the needle in a substantially aseptic condition. As the base of the device is painlessly moved into contact with the patient, adhesive pad 128 will grip the patient's skin so as to hold the device securely in position. The novel telescoping cover 153 can be constructed from various types of resilient plastic materials such as thermoplastic materials with low sliding friction that will permit the walls of the system to deform sufficiently to permit the telescoping segments to be telescoped in the manner shown in FIG. 26 upon a downward force being exerted on cover 136. Candidate materials for constructing cover assembly 153 include polyethylene, polypropylene and polycarbonate.

Turning next to FIGS. 27 through 37, still another form of the fluid delivery device of the invention is there shown and generally designated by the numeral 200. This device is similar in many respects to that shown in FIGS. 1 through 26 and like numerals are used in FIGS. 27 through 37 to identify like components. The primary difference between the earlier described embodiment and the embodiment of FIGS. 27 through 37 resides in the differently configured fluid flow control means and the totally different infusion means of the invention for infusing medicinal fluids into the patient. The details of construction of both of these novel features of the invention will presently be described.

As best seen in FIGS. 27 and 31, this latest form of the invention comprises two cooperating components, namely a fluid storage component 201 and a remotely located subcutaneous infusion component, which is identified in FIG. 31 by the numeral 220. Considering first the fluid storage component, this component comprises a base 202 having an upper surface 204 including a generally dome shaped central portion 204a and a peripheral portion 204b circumscribing central portion 204a. Base 202 is also provided with a lower surface 206 to which a patient interconnection means or adhesive pad assembly 208 of the general character previously described is connected.

A stored energy means cooperates with the upper surface 204 of base 202 to form a reservoir 210 having an inlet port 212, which is adapted to cooperate with a filling means of this latest form of the invention for filling reservoir 210 with the medicinal fluid to be infused into the patient. The stored energy means is here provided in the form of a laminate construction or assemblage 214 which is made up of first and second distendable membranes 214a and 214b (FIG. 29) which are here shown as coated, for specialized biocompatibility purposes, with a flurosilicone barrier material 214c. Membrane assemblage 214 is distendable as a result of pressure imparted on the membrane by fluids "F" introduced into reservoir 210 through inlet portion 212. As the membrane assemblage is distended in the manner shown in FIGS. 27 and 29, internal stresses will be established, which stresses tend to move the assemblage toward a less distended configuration and in a direction toward base 202.

Provided within the reservoir of the device, which is defined by the upper surface of the base and a concave surface 216a of a cover means for covering the distendable membrane, is ullage defining means for providing ullage within the reservoir and for engagement with membrane 214 as the membrane moves toward its less distended starting configuration. As before, the ullage defining means here comprises the dome shaped central portion 204a of base 202. When the distendable membrane after being distended, tends to return toward its less distended configuration, fluid contained within the reservoir 210 will flow uniformly outwardly of the reservoir through the novel infusion means of the invention for infusing the medicinal fluids into the patient.

Superimposed over base 202 is the cover means, shown here as a rigid cover 216, which is of the same general character as previously described, and through the use of novel sealing means, functions to sealably enclose membrane 214. The sealing means is identical to that previously described in connection with the embodiment shown in FIGS. 1 through 6.

The filling means of this latest form of the invention is quite similar in construction and operation to that shown in FIG. 1 and comprises a septum assembly 66 which is sealably disposed within fill port 212 formed in the intermediate portion of base 202 (see FIG. 12). Septum assembly 66 includes an elastomeric pierceable core 66b which is sealably disposed within a core housing 66a. As best seen in FIG. 27, septum assembly 66 is disposed proximate the upper end of a fill adapter which is similar to that previously described in connection with FIGS. 1 through 6. However, as best seen in FIG. 27, the fill adapter 215 includes an upper tapered wall portion 215a which functions to guide the syringe needle 76 precisely toward a very small opening 215b formed proximate core 66b. With this construction, when the lower portion of the adapter is broken away from the base 202, reinsertion of the syringe needle without the benefit of the guiding wall 215a would be most difficult, thereby effectively preventing refilling of reservoir 210.

The filing syringe component of the filling means of this latest form of the invention, is identical to that previously described and the upper part of the filling syringe is receivable within the lower portion 215c of fill adapter 215 in the same manner as depicted in FIG. 4.

As previously mentioned, the infusion means of this latest form of the invention is totally different in construction and operation from that shown in FIGS. 1 through 26. More particularly, this novel infusion means here comprises an administration set 219 having a subcutaneous infusion device 220 (FIG. 31) and connector means for operably interconnecting device 220 with the fluid reservoir 210 of the fluid delivery device. As best seen in FIGS. 31, 32, and 33, the connector means here comprises a connector boss 222 and a length of tubing 224 which interconnects device 220 with boss 222 (FIG. 31). Connector boss 222 is sealably received within a connector boss receiving port 226 formed in base 202 and cover 216 (FIG. 27) in the manner so as to place tubing 224 in communication with a flow passageway 228 formed in a flow plate 229 which is connected to base 202 by any suitable means such as sonic welding. For this purpose, sonic energy directors 229a are provided on plate 229 to aid in the sonic welding step (see FIGS. 27 and 28). Passageway 228 is, in turn, in communication with reservoir 210 via first flow control means here provided as a rate control assembly 240 which is housed within a cavity 242 formed in an elastomeric holding sleeve 242a disposed in base 202 proximate the outlet 210a of reservoir 210. Assembly 240, which is of the configuration shown in FIG. 27a, comprises a porous base 244, a wafer-like element or wafer 246 and a filter 248. Wafer 246, which can be constructed from various metals and plastics, has a centrally disposed, laser drilled microbore 246a (for example, one micron to 50 microns in diameter), which precisely controls fluid flow from reservoir 210 toward the administration set 219. Wafer-like element 246 which is a very thin film material (for example 0.010 to 0.030 inches) can be constructed from various materials including a polyamide material sold by duPont under the name and style KAPTON. In a manner presently to be described, element 246 cooperates with a second flow control means provided in the form of a porous frit-like element 247 (FIG. 34) to precisely control fluid flow from the apparatus of the invention.

Turning particularly to FIGS. 31, 32, and 33, the details of construction of the subcutaneous infusion set 219 is there shown. Infusion device 220 of the administration set here comprises a base 245 having upper and lower surfaces 245a and 245b and a generally circular shaped opening 249. Connected to base 245 is a cover 251. Cover 251 and base 245 cooperate to define an internal chamber 250 within which a generally spiral shaped cannula 252 is dynamically mounted. Cannula 252 includes a circuitously shaped body portion 252a which is disposed within chamber 250 and a stem portion 252b which is mounted between base 245 and cover 251 in a manner presently to be described. Disposed within stem portion 252b is the previously mentioned second fluid flow control means of the invention, which here comprises an elongated, generally cylindrically shaped flow control element 247. Element 247 cooperates with the first flow control means or assemblage 240 to precisely regulate fluid flow from the device. Element 247 can be constructed from various materials including porous ceramic, plastic and metal. Cannula 252 also includes an outlet end, here provided in the form of a needle-like segment 252c, which extends generally perpendicularly downward from lower surface 245b of base 245 for subdermal infusion of medicinal fluids into the patient. For this purpose, segment 252c is provided with a sharp, pointed extremity 252d (see FIG. 34).

As shown in FIG. 33, stem portion 252b of the very small diameter spiral cannula 252 is encased within the inboard end 224a of fluid delivery tube 224 and the assembly thus formed is uniquely supported between a stem portion 251a of cover 251 (FIG. 33) and base 245 by a cannula encapsulation means shown here as a standard potting compound 255 (FIG. 33). Compound 255 rigidly supports the inboard end of tube 224 and portion 252b of the cannula so as to provide a secure interconnection of the cannula with base 245 and cover 251. As best seen in FIG. 34, portion 252b of the cannula is provided with a bend 252e to better secure the assemblage in place. Secondary flow control means or frit 247 is disposed upsteam of and separated from bend 252e.

Referring to FIG. 34A, an alternate form of cannula and secondary flow control means is shown. Here cannula 252 is provided with an enlarged diameter collar 252f which houses porous flow control frit 247. Frit 247 can be secured within collar 252f by various joining methods including adhesive weldment. Collar 252f is preferably secured to the cannula body by plasma weldment.

Surrounding portion 252c of cannula 252 is a novel crushable cover assembly 253 which is of the construction shown in FIG. 35. Assembly 253 comprises a crushable foam body 253a and a peel away cover 253b. Peel away cover 253b protects a thin layer of adhesive which functions to bond body 253a to the lower surface of cover 251 of the infusion device (FIG. 33). Surrounding body 253a is a protective sheath 257 of the character shown in FIG. 36. The function of cover assembly 253 and materials used to construct the assembly will be described in greater detail in the paragraph which follows.

In using the device of this latest form of the invention, after the reservoir has been filled and the administration set has been suitably interconnected with the fluid delivery portion of the apparatus by means of delivery tube 224 in the manner shown in FIG. 31, infusion device 220 can be interconnected with the patient for subdermal delivery of fluids from the fluid delivery portion of the apparatus. This is accomplished by breaking away adapter 215 so as to present a smooth lower surface on the fluid storage component so that it can be connected to the patient and by removing protective sheath 257 so that the subcutaneous infusion component can be connected to the patient at a location remote from the fluid storage component.

Figure 37:
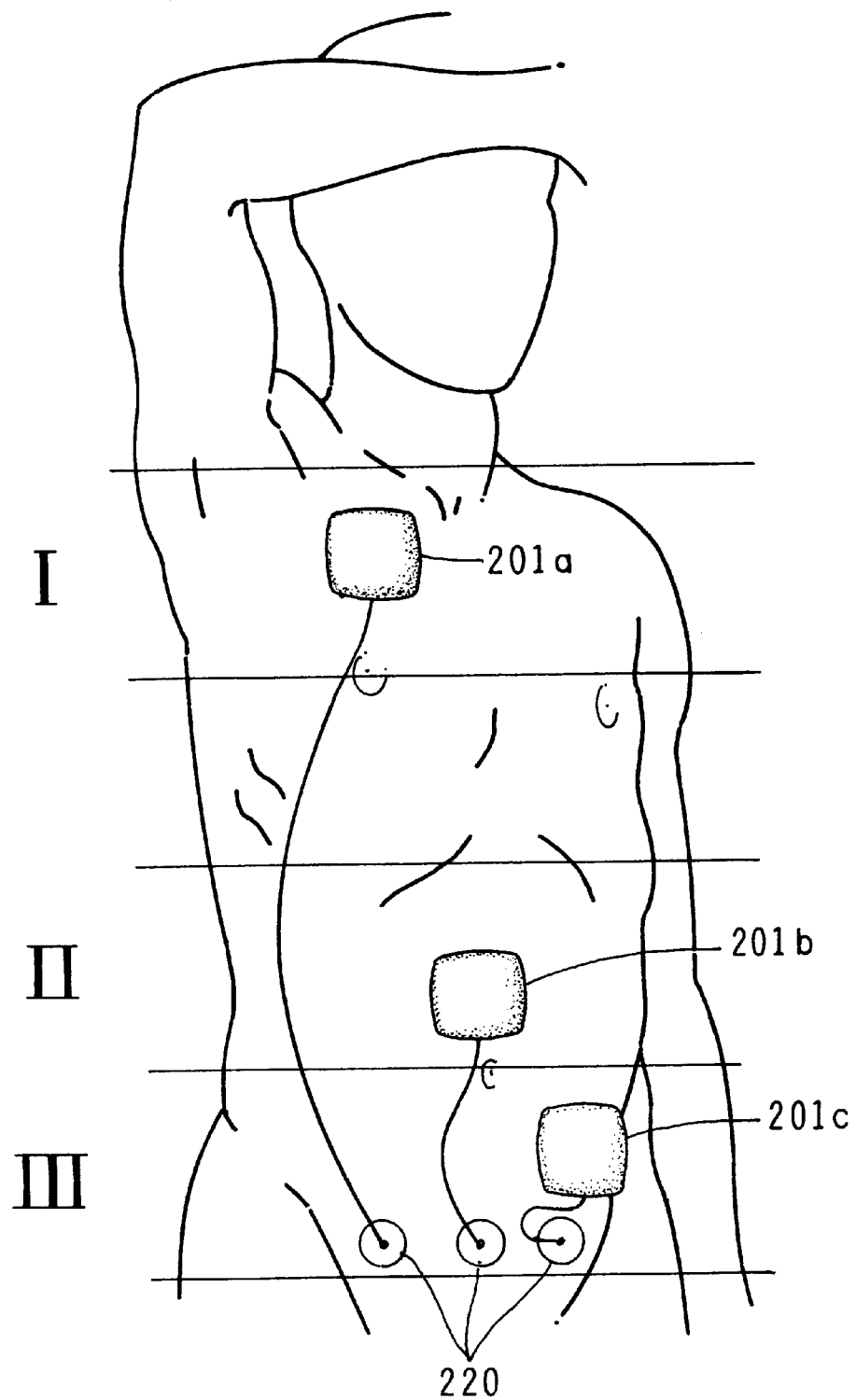
FIG. 37 is a generally illustrative view showing the various locations at which the infusion means can be affixed to the patient.

Referring to FIG. 37 there is shown, by way of example, three possible locations for affixing the storage component of the invention and three possible locations for affixing the subcutaneous infusion component to the patient. In some instances, the choice of location of the larger, more bulky storage component may be simply a matter of convenience. In other cases, particularly with small patients, since the infusion component, is lighter and occupies a much smaller surface area on the patient, the patient can select optimum infusion sites at locations on the torso where affixation of the storage component is impractical. For example, as shown in FIG. 37, the storage component 201a is located on the chest of the patient, while storage component 201b is located on the stomach and storage component 201c is located just below the belt line. In all cases, the subcutaneous infusion component 220 can be comfortably and conveniently positioned just above the pelvic area where there generally is an area of pronounced subdermal fat.

Interconnection of the subcutaneous infusion component of the apparatus is accomplished by pressing the now exposed base 253c of crushable cover body 253a against the patient's skin "S" (see FIG. 33). A downward force exerted against cover 251 will cause crushable body 253a to collapse into chamber 250 in the manner shown in FIG. 33 allowing the needle portion 252d of the cannula to penetrate the patient's skin and tissue in the manner shown in FIG. 33. This unique construction of the needle cover enables the patient to use the device without being aware of the insertion of the needle into the skin while at the same time maintaining the needle in a substantially aseptic condition. The highly novel crushable cover body 253a can be constructed from various materials including a low density open cell foam such as a hydrophilic polyurethane product sold by Hampshire Chemical Corporation of Lexington, Mass. under the name and style HYPOL. Body 253a could also be constructed from a low density hydrophobic foam, such as polyisoprene, from a soft polymer gel or a hydrophobic gel that is swollen with mineral oil and from pl 69 like materials.

It is to be noted that an extremely important aspect of the infusion device 220 resides in the novel design of the circuitous cannula 252 and its unique interconnection with the base 245 and cover 251 of the infusion device. With the highly novel construction shown in the drawings, when the device is connected to the patient, in the manner shown in FIG. 33, with the needle portion 252c of the cannula penetrating the patient's body as, for example, the patent's abdomen (see also FIG. 37), increased patient comfort is provided since normal movement by the patient will permit the cannula to move within chamber 250 while the base remains completely stationary. Without this important feature, normal movements by the patient causing flexing of the muscle and tissue could cause needle necrosis, irritation and discomfort to the patient with prolonged use.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

What is claimed is:

1. A fluid delivery device for infusing medicinal fluids into a patient at a controlled rate comprising:
   (a) a base having a lower surface and a fill port;
   (b) stored energy means for forming, in conjunction with said base, a reservoir having an inlet port and an outlet port, said stored energy means comprising at least one distendable membrane superimposed over said base, said membrane being distendable as a result of pressure imparted by liquids introduced into said reservoir to establish internal stresses, said stresses tending to move said membrane toward a less distended configuration;
   (c) cover means connected to said base for covering said distendable membrane;
   (d) filling means connected to a selected one of said base and said cover for filling said reservoir; and
   (e) infusion means connected to and supported by said base for infusing into the patient liquids introduced into said fluid reservoir, said infusion means comprising:
      (i) a hollow cannula extending downwardly from said base; and
      (ii) a non-resilient, collapsible cover surrounding said hollow cannula, said cover being collapsible from an expanded configuration extending outwardly from said lower surface of said base to a collapsed configuration wherein said lower surface thereof remains substantially coplaner with said base.

2. A device as defined in claim 1 in which said collapsible cover comprises a non-resilient collapsible foam material.

3. A device as defined in claim 1 further including flow control means disposed between said reservoir and said infusion means for controlling fluid flow from said reservoir.

4. A fluid delivery device for infusing medicinal fluids into a patient at a controlled rate comprising:
   (a) a base having a lower surface and an upper surface including a central portion and a peripheral portion circumscribing said central portion, said peripheral portion having a fill port formed therein;
   (b) stored energy means for forming, in conjunction with said base, a reservoir having an inlet in communication with said fill port and an outlet port, said stored energy means comprising at least one distendable membrane superimposed over said base, said membrane being distendable as a result of pressure imparted by liquids introduced into said reservoir to establish internal stresses, said stresses tending to move said membrane toward a less distended configuration;
   (c) infusion means for infusing medicinal fluids from said fluid reservoir into the patient, said infusion means comprising:
      (i) a hollow needle having an inlet in communication with said outlet port of said reservoir and terminating in a piercing point; and
      (ii) a non-resilient, collapsible cover initially surrounding and substantially encapsulating said hollow needle, said cover having a lower surface and being collapsible from an expanded configuration surrounding said needle to a collapsed configuration wherein said hollow needle extends from said lower surface of said cover, said lower surface of said cover being substantially coplanar with said lower surface of said base;

(d) cover means connected to said base for covering said distendable membrane; and (e) filling means connected to said base for filling said reservoir, said filling means comprising:
   (i) a pierceable septum sealably disposed within said fill port of said base; and
   (ii) a fill adapter connected to said peripheral portion of said base, said fill adapter including an enlarged diameter portion and a reduced diameter neck portion, at least a part of said fill adapter being separable from said base; and
   (iii) a container telescopically receivable within said enlarged diameter portion of said fill adapter.

5. A device as defined in claim 4 in which said collapsible cover comprises a non-resilient crushable foam.

6. A device as defined in claim 4 further including ullage defining means disposed within said reservoir, said ullage means comprising a dome-shaped protuberance formed on said base.

7. A fluid delivery device for infusing medicinal fluids into a patient at a controlled rate comprising:
   (a) a base having a lower surface and an upper surface including a central portion and a peripheral portion circumscribing said central portion, said peripheral portion having a fill port formed therein;
   (b) stored energy means for forming, in conjunction with said base, a reservoir having an inlet and an outlet port, said stored energy means comprising at least one distendable membrane superimposed over said base, said membrane being distendable as a result of pressure imparted by liquids introduced into said reservoir to establish internal stresses, said stresses tending to move said membrane toward a less distended configuration;
   (c) infusion means for infusing medicinal fluids from said fluid reservoir into the patient, said infusion means comprising:
      (i) a hollow needle having an inlet in communication with said outlet port of said reservoir and terminating in a piercing point; and
      (ii) a non-resilient, collapsible cover surrounding and initially substantially encapsulating said hollow needle, said cover having a lower surface and being collapsible from an expanded configuration surrounding said needle to a collapsed configuration wherein said hollow needle extends from said lower surface of said cover, said lower surface being substantially coplanar with said lower surface of said base;
   (d) cover means connected to said base for covering said distendable membrane;
   (e) filling means connected to said base for filling said reservoir, said filling means comprising:
      (i) a septum assembly, including a pierceable septum sealably disposed within said fill port of said base;
      (ii) a fill adapter connected to said peripheral portion of said base, said fill adapter including an enlarged diameter portion and a reduced diameter portion at least a part of said fill adapter being separable from said base;
      (iii) a container telescopically receivable within said enlarged diameter portion of said fill adapter, said container having a container reservoir and a plunger telescopically movable within said container reservoir;
      (iv) pusher means receivable over said fill adapter and movable relative thereto for moving said plunger within said container reservoir; and
   (f) flow control means disposed between said reservoir defined by said stored energy means and said infusion means for controlling fluid flow from said reservoir, said flow control means comprising a porous element.

8. A device as defined in claim 7 further including ullage defining means disposed within said reservoir, said ullage means comprising a dome-shaped protuberance formed in said base.

9. A fluid delivery device for infusing medicinal fluids into a patient at a controlled rate comprising:
   (a) a base having a lower surface and a fill port;
   (b) stored energy means for forming, in conjunction with said base, a reservoir having an inlet port and an outlet port, said stored energy means comprising at least one distendable membrane superimposed over said base, said membrane being distendable as a result of pressure imparted by liquids introduced into said reservoir to establish internal stresses, said stresses tending to move said membrane toward a less distended configuration;
   (c) cover means connected to said base for covering said distendable membrane;
   (d) filling means connected to one of said base and said cover for filling said reservoir; and
   (e) infusion means operably interconnected with said base for infusing into the patient liquids introduced into said fluid reservoir, said infusion means comprising:
      (i) a hollow cannula; and
      (ii) a non-resilient collapsible cover initially surrounding said hollow cannula, said cover having a lower surface and being collapsible from an expanded configuration surrounding said needle to a collapsed configuration wherein said hollow needle extends from said lower surface of said cover, said lower surface of said cover being substantially coplanar with said lower surface of said base; and
   (f) flow control means disposed between said reservoir and said infusion means for controlling fluid flow into the patient.

10. A device as defined in claim 9 in which said collapsible cover comprises a non-resilient collapsible foam material.

11. A device as defined in claim 10 in which said flow control means comprises a wafer having a microbore therethrough.

12. A device as defined in claim 9 in which said infusion means is connected to and supported by said base, said hollow cannula extending downwardly from said base.

13. A fluid delivery device for infusing medicinal fluids into a patient at a controlled rate comprising:
   (a) a base having a lower surface and a fill port;
   (b) stored energy means for forming, in conjunction with said base, a reservoir having an inlet port and an outlet port, said stored energy means comprising at least one distendable membrane superimposed over said base, said membrane being distendable as a result of pressure imparted by liquids introduced into said reservoir to establish internal stresses, said stresses tending to move said membrane toward a less distended configuration;
   (c) cover means connected to said base for covering said distendable membrane;
   (d) filling means connected to said base for filling said reservoir, said filling means comprising:

(i) a septum assembly, including a pierceable septum sealably disposed within said fill port of said base;

(ii) a filling syringe having a housing, a fluid reservoir within said housing, and a hollow cannula carried by said housing for communication with said fluid reservoir; and (iii) a fill adapter connected to said lower surface of said base and extending outwardly therefrom, said fill adapter including a wall portion defining an opening for closely receiving at least a portion of said housing of said filling syringe; and (e) infusion means operably interconnected with said base for infusing into the patient liquids introduced into said fluid reservoir, said infusion means comprising:

(i) a hollow cannula; and (ii) a non-resilient collapsible cover surrounding said hollow cannula, said cover having a lower surface and being collapsible from an expanded configuration surrounding said needle to a collapsed configuration wherein said hollow needle extends from said lower surface of said cover, said lower surface of said covering being substantially coplanar with said lower surface of said base.

14. A device as defined in claim 13 further including flow control means disposed between said reservoir and said infusion means for controlling fluid flow from said reservoir.

15. A device as defined in claim 13 further including ullage defining means disposed within said reservoir for providing ullage within said reservoir, said ullage defining means comprising a dome shaped protuberance formed on said base.

16. A device as defined in claim 13 in which said hollow cannula of said infusion means is connected to and supported by said base.

17. A device as defined in claim 13 in which said collapsible cover comprises a non-resilient collapsible foam material.

18. A fluid delivery device for infusing medicinal fluids into a patient at a controlled rate comprising:

(a) a base having a lower surface and a fill port;

(b) stored energy means for forming, in conjunction with said base, a reservoir having an inlet port and an outlet port, said stored energy means comprising at least one distendable membrane superimposed over said base, said membrane being distendable as a result of pressure imparted by liquids introduced into said reservoir to establish internal stresses, said stresses tending to move said membrane toward a less distended configuration;

(c) cover means connected to said base for covering said distendable membrane;

(d) filling means connected to a selected one of said base and said cover for filling said reservoir, said filling means comprising:

(i) a septum sealably mounted within said fill port of said base; and (ii) a fill adapter removably connected to said base proximate said fill port of said base, said fill adapter including an enlarged diameter portion and a reduced portion, said reduced diameter portion having a serration to enable a portion of said fill adapter to be broken away from said base; and (e) infusion means connected to and supported by said base for infusing into the patient liquids introduced into said fluid reservoir, said infusion means comprising:

(i) a hollow cannula extending downwardly from said base; and (ii) a collapsible cover surrounding said hollow cannula.

\* \* \* \* \*